(12) United States Patent
Ilin et al.

(10) Patent No.: US 10,251,939 B2
(45) Date of Patent: Apr. 9, 2019

(54) ANTIBACTERIAL AGENT FOR TREATING INFECTIOUS DISEASES OF BACTERIAL ORIGIN

(71) Applicant: "Scientific Center of Anti-Infectious Drugs" Joint-Stock Company, Almaty (KZ)

(72) Inventors: Alexandr Ivanovich Ilin, Almaty (KZ); Murat Esengalievich Kulmanov, Almaty (KZ)

(73) Assignee: "SCIENTIFIC CENTER OF ANTI-INFECTIOUS DRUGS" JOINT-STOCK COMPANY, Almaty (KZ)

( * ) Notice: Subject to any disclaimer, the term of this patent is extended or adjusted under 35 U.S.C. 154(b) by 0 days.

(21) Appl. No.: 14/850,167

(22) Filed: Sep. 10, 2015

(65) Prior Publication Data

US 2015/0374837 A1 Dec. 31, 2015

Related U.S. Application Data

(62) Division of application No. 13/994,631, filed as application No. PCT/KZ2011/000019 on Dec. 9, 2011, now Pat. No. 10,149,890.

(30) Foreign Application Priority Data

Dec. 30, 2010 (KZ) .................................. 2010/1816

(51) Int. Cl.
| | | |
|---|---|---|
| A61K 9/51 | (2006.01) | |
| A61K 38/38 | (2006.01) | |
| A61K 45/06 | (2006.01) | |
| A61K 38/20 | (2006.01) | |
| A61K 38/21 | (2006.01) | |
| A61K 33/18 | (2006.01) | |
| A61K 47/54 | (2017.01) | |
| A61K 47/64 | (2017.01) | |

(52) U.S. Cl.
CPC .......... *A61K 38/2013* (2013.01); *A61K 33/18* (2013.01); *A61K 47/549* (2017.08); *A61K 47/643* (2017.08)

(58) Field of Classification Search
None
See application file for complete search history.

(56) References Cited

FOREIGN PATENT DOCUMENTS

| EP | 0978289 A1 | 2/2000 | |
|---|---|---|---|
| KZ | 15116 | 12/2004 | |
| KZ | 15116 A | * 12/2004 | |
| KZ | 015116 A1 | * 12/2004 | |
| RU | 2157405 | 10/2000 | |
| WO | WO-96/39839 A1 | 12/1996 | |
| WO | WO 0178751 A1 | * 10/2001 | ............. A61K 33/18 |

OTHER PUBLICATIONS

Solomon.The definition and unit of ionic strength. Journal of Chemical Education; 78(12):1691-1692.*
Davtyon et al. Design of Iodine-Lithium-alpha-Dextrin Liquid Crystal with Potent Antimicrobial and Anti-Inflammatory Properties. Current Pharmaceutical Design, 2009; 15:1172-1186.*
Ju et al. Structure-Function Analysis of Human Interleukin-2. Journal of Biological Chemistry, 1986; 262(12):5723-5731.*
Interleukin-1 beta (163-171), Found from the Internet: <URL:http://pubchem.ncbi.nlm.nih.gov/summary/summary.cgi?cid=123872&loc=ec_rcs>./, p. 1-4, Aug. 9, 2005.
Database, GenBank, AAA59134, Jun. 1, 1995, Found from the Internet: < URL: http://www.ncbi.nlm.nih.gov/ protein/AAA59134. 1, p. 1-2, Found Apr. 24, 2012.
Nimz et al., An orthorhombic crystal form of cyclohexaicosaose, CA26.32.59 H(2)O: comparison with the triclinic form., *Carbohydrate Research*, 2001, pp. 141-153.
Noltemeyer et al., *J.AM. Chem. Soc.*, Topography of cyclodextrin inclusion complexes. 12. Structural chemistry of linear .alpha.-cyclodextrin-polyiodide complexes. X-ray crystal structures of (.alpha.-cyclodextrin)2.LiI3.I2.8H2O and (.alpha.-cyclodextrin)2.Cd0.5).I5.27H2O. Models for the blue amylose-iodine complex1980, pp. 2710.
Noltemeyer et al., X-ray studies of linear polyiodide chains in α-cyclodextrin channels and a model for the starch-iodine complex *Nature*, 1976, pp. 629.
Goldgur et al., Structure of the HIV-1 integrase catalytic domain complexed with an inhibitor: A platform for antiviral drug design, *Proc. Natl. Acid. Sci USA*, 1998, pp. 9150-9154.
Dyda et al., Crystal structure of the catalytic domain of HIV-1 integrase: similarity to other polynucleotidyl transferases., *Science*, 1994 pp. 1981-1986.

(Continued)

*Primary Examiner* — Vanessa L. Ford
*Assistant Examiner* — Sandra E Dillahunt
(74) *Attorney, Agent, or Firm* — Leason Ellis LLP

(57) ABSTRACT

The invention relates to medicine, namely to the antimicrobial agent for the treatment of infectious bacterial diseases including hospital infections and drug-resistant TB which represents the ion nanostructured complex (INSC) synthesized from carbohydrates proteins and/or polypeptides (albumins, interleukins, interferons, signaling proteins, etc), which are to enhance the antimicrobial activity in vivo, by activating immune cells that contain at least one terminal amino acid such as Phe, Ala, Val, Ala, Leu, Ile, and others with electron-donor functional groups, iodine and halides of the alkali and alkaline earth elements in the fourth stage at a certain ionic strength; an antibacterial agent increases: the susceptibility of bacteria, including antibiotic-resistant, to antibiotics; activity of monocytes and macrophages; efficiency of antibiotic treatment of hospital infections and drug-resistant TB; it also has antiviral activity, stimulates hematopoietic function of bone marrow; has an antitumor effect and radioprotective properties; in acceptable concentrations of components can be used as non-pharmaceutical agent (BAFS or parapharmaceutical); is presented in the pharmacological form suitable for parenteral, oral, external, or other application. INSC has the formula [{(Ln (MeI3)+) y [Me (Lm) I]+x} (Cl—) y+x+k] with M=30-300 kDa.

8 Claims, 11 Drawing Sheets

(56) References Cited

OTHER PUBLICATIONS

Pearson, R.G., Hard and Soft Acids and Bases, *Journal of the American Chemical Society*, 1963, 85, pp. 3533-3539.
Pearson, R.G., Hard and Soft Acids and Bases, HSAB. Part II. Underlying theories, *Journal of Chemical Education*, 1968, 45, pp. 643-648.
Pearson, R.G., Failure of Pauling's Bond Energy Equation, *Chemical Communications*, 1968, pp. 68-67.
Gehlen H.Z., Physical Chemistry, 1954, 2013, pp. 125-136.
International Search Report and Written Opinion of the International Searching Authority dated May 4, 2012 for the corresponding PCT Application No. PCT/KZ/000019.
International Preliminary Report on Patentability dated Jul. 2, 2013 for the corresponding PCT Application No. PCT/KZ/000019.

* cited by examiner

1A – nanocrystals of FS-1, magnification 400×; 1B – nanocrystals of FS-1, magnification 40000×.

FS-1 electron microphotographs

2A – microcrystals of FS-1, magnification 5000×; 2B – microcrystals of FS-1, magnification 12000×.

FS-1 electron microphotographs

Electron microphotographs of FS-1 monocrystals

Electron microphotographs of FS-1 crystals with various sizes

Dependence of formation of the triiodide ion calcium complex with carbohydrates on the ionic strength Dependence of formation of the triiodide ion magnesium complex with carbohydrates on the ionic strength I structure
E=-106,01kcal/mol II structure
ΔE=-79,12kcal/mol III structure
ΔE=-88,86kcal/mol Formation of stable coordination substances in the carbohydrate-protein-salt LiCl, MgCl$_2$ system.

Interaction of molecular iodine with lithium galogenides, carbohydrates, terminal amino acides triplets of protein Example 1 – FS-1.1

Example 2 – FS-1.2

Example 3 – FS-1.3

Example 4 – FS-1.4

Example 6 – FS-1.5

Example 7 – FS-1.6

Example 8 – FS-1.7

Example 9 – FS-1.8

Optical microphotografs of FS-1 examples 1-4 and 6-9

Optical microphotograf of FS-1 example 5 (FS-1)

Dynamics of survival of rats in the control and experimental groups within 30 days after irradiation: 1) irradiation dose of 800 R, 2) irradiation dose of 800 R against oral administration into the body of 1,0 ml of PKh 30 minutes before irradiation.

ANTIBACTERIAL AGENT FOR TREATING INFECTIOUS DISEASES OF BACTERIAL ORIGIN

CROSS-REFERENCE TO RELATED PATENT APPLICATIONS

This application is a Divisional of U.S. application Ser. No. 13/994,631, filed Jun. 14, 2013, which is a U.S. National Phase Application under 35 U.S.C. § 371 of International Patent Application No. PCT/KZ2011/000019, filed Dec. 9, 2011 which claims priority to Kazakhstan Application No. 2010/1816.1, filed Dec. 30, 2010, which are hereby incorporated by reference in their entireties. The International Application was published as International Publication No. WO 2012/091534 under PCT Article 21(2).

FIELD OF THE DISCLOSURE

The disclosure relates to medicine, namely pharmaceutics, and may be used for treating diseases of bacterial origin, especially in treating diseases caused by drug-resistant strains of microbes, and bacterial and viral (mixed) infections.

BACKGROUND

Methods and means to damage pathogenic bacteria in the present are antibiotics which combine all medications that suppress activity of infectious agents such as bacteria, fungi, and protozoa.

However, due to increased drug resistance of infectious agents to the known groups of antibiotics, the problem of development of new antimicrobial drugs has not lost its relevance.

Thus, for example, worldwide there is an increase in tuberculosis incidence rate and increase in mortality observed, caused by drug-resistant pathogens. Resistance to antituberculosis drugs was found in all 35 surveyed countries and regions, indicating that the problem is global.

Polyresistance to antituberculosis drugs is the most difficult form of drug-resistance, known at present. According to WHO, since the early 90-ies in different regions of the planet several outbreaks of multidrug-resistant tuberculosis have been reported.

It is known that molecular iodine can easily pass through bi-lipid cell membranes of microorganisms and penetrate into a cell. Antimicrobial action of iodine compound is due to the ability of iodine (elemental iodine, hypoiodine acid, iodine cation) to interact with $NH_2$-groups of amino acids (lysine, histidine, arginine, etc.), as well as nucleotides (adenine, cytosine, guanine) forming N-iodine derivatives. In addition, there is an oxidation of SH-groups of cysteine taking place, resulting in disruption of protein synthesis. Interaction with phenolic groups of iodine tyrosine leads to breaking of hydrogen bonds in these amino acids. Affecting double carbon bonds of unsaturated fatty acids, iodine thereby changes the properties of lipids.

The ability of iodine to easily penetrate through cell membranes makes its application more valuable for those infections, the main development of which takes place in intracellular structures (brucellosis, clamidiosis, hepatitis, etc.).

There is a known drug Yodomidol, with bactericidal and virucidal activity, containing iodine, potassium or sodium iodide, synthetic water-soluble polymer, natural polymers such as polysaccharides and mono- and oligosaccharides, in the following ratio, g/L:

| | |
|---|---|
| iodine | 6-10 |
| potassium iodide | 9-15 |
| synthetic water-soluble polymer | 2-4 |
| natural polymer (polysaccharides) and mono- and oligosaccharides | 8-120 |
| water | Balance |

(KZ 6730B, 16 Nov. 1998).

Disadvantage of this drug is its relatively high toxicity.

There is a known virulicidal pharmaceutical product (EP 0978289 A1, 2 Sep. 9, 2000), with antiviral activity, which contains iodine, potassium or sodium iodide, synthetic water-soluble polymer, a mixture of natural mono-, oligo- and polysaccharides and lithium chloride with the following components ratio, g/L:

| | |
|---|---|
| iodine ЙОД | 0.8-25 |
| potassium iodide | 1.2-38 |
| lithium chloride | 0.1-20 |
| synthetic water-soluble polymer | 0.01-6 |
| mono-, oligo- and polysaccharides | 8-400 |
| water | Balance |

There is a known bactericidal and virucidal pharmaceutical product for prevention and treatment of mono- and mixed infections, including tuberculosis, brucellosis, plague, hepatitis, HIV, containing a pool of proteins and/or halogenated proteins, carbohydrates and/or halogen-derivative carbohydrates, synthetic water-soluble polymer, lithium chloride, potassium or sodium iodide, iodine, water or saline solution in the following ratio (g/L):

| | |
|---|---|
| pool of proteins and/or halogenated proteins | From 0.01 to 200 |
| carbohydrates and/or halogen-derivative carbohydrates | From 0.01 to 450 |
| synthetic water-soluble polymer | From 0.01 to 100 |
| lithium chloride | From 0.01 to 200 |
| potassium or sodium iodide | From 0.01 to 300 |
| iodine | From 0.01 to 200 |
| water or saline solution | to 1 L |

(KZ 15116A, 15 Dec. 2004).

Bactericidal and virucidal pharmaceutical agent represents a complex physical-chemical system, formed by mono- and polyfunctional ligands (anions, proteins, carbohydrates, synthetic water-soluble polymers) and acids (iodine, alkali metal cations), which is in pseudo-equilibrium state. In this system, there are adjoint complexation, association and dissociation processes taking place. A sequence of processes of acid-base interactions; chemical nature of the polyfunctional ligands (proteins, carbohydrates, water-soluble synthetic polymers) involved in them, the presence in the process of ligands with different molecular weight (e.g. mono-, oligo- and polysaccharides) results in structure formation in the system, and thus it acquires all properties of a colloidal system.

The presence of pharmaceutical iodine in the composition not only enhances bactericidal and virucidal properties due to those of iodine itself, but it also ensures a synergistic effect of each active substance individually and of all of them together present in the agent in balanced concentrations.

This product contains halogen derivative compounds: halogenated proteins and halogenated carbohydrates.

There is a known iodine complex of alkylpolyglycosides (WO 9639839 A1, 19 Dec. 1996) containing (in % wt.) from 0.5 to 30 of iodine; from 0.2 to 14 of iodide in the form of salt; acids or their blends, and from 2 to 85 of sugar surfactant selected from the group of sugars containing alkyl glucose ether, aldobionamide, glycinamide, glyceramide, glyceroglulipoid, fatty polyhydroxy acids amides, alkylpolyglucocides with general formula $R_1O(R_2O)b(Z)a$, where $R_1$—monovalent organic radical of from 6 to 30 carbon atoms; $R_2$—divalent alkylene radical having from 2 to 4 carbon atoms; Z—sugar derivative containing 5 or 6 carbon atoms; b—natural number from 0 to $I_2$, and a—natural number from 1 to 6.

There is a known method for producing immobilized enzymes through complexation reaction with molecular iodine and potassium iodide (RU 2157405 C2); as a result of complexation reaction, proteins are produced that contain bound iodine, and which from a solution pass to a solid phase state, i.e. water-insoluble complexes are formed. Solid phase state is characterized by the formation of polydisperse particles ranging in size from several micrometers to tens or hundreds of microns, which (the particles), in view of the large total surface area of zymophore able to interact with molecules of microbial substrates, ensure antimicrobial action of immobilized enzymes. Iodine that is a part of the complex provides a microbicide effect.

There is a known drug for administration of antiseptic agents, including halogen, into lower respiratory tract, containing at least one antiseptic in combination with support in the form of particles, obtained by known methods, and the carrier contains at least one liposomal preparation, microspheres sample, nanoparticles preparation, large porous particles preparation or molecules preparation, coated with polymer using a pulsating laser ranging in size from 1 to 30 microns (Patent RU 2212884 C2).

In all of the above known patents, authors did not set the task of synthesizing complex compounds with a given structure and properties, or excreting complex compounds from solutions and determining their composition and physical-chemical properties, which makes it hard to use complex iodine compounds with carbohydrates and proteins with biocidal properties as medicinal products. Moreover, the development of appropriate dosage forms, without a specific set of properties and qualities of complex iodine compounds—antibacterial agents, characterized by physical and chemical properties and composition, is hindered.

In recent years, some works devoted to exploration of the structure of complex compounds of carbohydrates with salts of magnesium, calcium and other complexing agents have appeared in scientific literature (O. Nimz, K. Geßler, I. Uson, W. Saenger//*Carbohydrate Research* 2001. V 336. P. 141-153.; M. Noltemeyer, W. Saenger//*JACS* 1980. V. 102: 8.9. P. 2710.; M. Noltemeyer, W. Saenger//*Nature*. 1976. V259.26. P. 629).

Crystalline structure of a whole number of enzymes with having in its composition ions of magnesium, potassium, calcium, lithium, in their composition, i.e., metal salts, has been established. (Y. Goldgur, F. Dyda, A. B. Hickman, T. M. Jenkins, R. Craigie, D. R. Davies//*Proc. Natl. Acid. Sci USA* 1998. V95. N°16. P. 9150-9154.; F. Dyda, A. B. Hickman, T. M. Jenkins, A. Engelman, R. Craigie, D. R. Davies//*Science*. 1994. V266. P. 1981-1986).

At the same time there are no works involving a purposeful synthesis of iodine coordination compounds with a tailored nanoscale structure and, accordingly, tailored biocidal properties, suitable for implementation of a mechanism of action of these compounds.

Thus, the object of this invention is to create antibacterial agent (ABA) for the treatment of diseases of bacterial origin, including hospital acquired diseases and drug resistant TB.

Additional objectives of this invention are to develop a method for preparation of antibacterial agent and ABA-based drug to treat infectious diseases of bacterial origin.

Technical result of the invention is the increase ABA efficiency in vivo through activation of immunocompetent cells.

SUMMARY

The technical result is accomplished through the developed ABA, which represents an ionic nanostrutured complex (INSC), formed by proteins and/or carbohydrates, metal salts and iodine intercalated into them, while to obtain an ordered structure of antimicrobial agent and the necessary immunotropic action, the complexation reaction is conducted in four stages—first is interaction of carbohydrates and proteins with metal salts; second step is intercalation of 5-95% of the required amount of iodine into a complex formed during the first stage of complexation reaction at a certain ionic strength; third stage is introduction in the complexing reaction of proteins containing at least one chain-terminal amino acid with electron-donating functional groups and a specific site, accounting for a required immune response, and the fourth stage is intercalation of the remaining amount of iodine in antibacterial agent.

In addition, according to the invention, an ABA was proposed, which, despite the fact that it has a weak antitumor activity, a weak radioprotective effect, however, in conjunction with the unique ability to recover hematopoietic function of bone marrow, could be of great practical importance for the prevention of possible adverse effects of chemo- and radiotherapy in accompanying complex drug therapy of tumors.

Another technical result is accomplished by the fact that proteins and/or polypeptides that are part of the ABA, have immunogenic activity and contain at least one terminal amino acid with electron-donating functional groups, which—when ABA is administered into body, anchor in the area of stimulating and costimulating receptors of immunocompetent cell through chain-terminal amino acids possessing hydrophobic and electron-donor functional groups, and specific sites of these proteins activate immunocompetent cells of the first and the second lines of defense—monocytes-macrophages and cytotoxic T-lymphocytes.

Further, the invention includes a pharmaceutical form of the claimed ABA

Depending on the specific proposed application, the pharmaceutical composition according to the present invention can be prepared in the form of a solution, suspension, parenteral composition, ointment, cream, aerosol, powder, tablets, capsules, or other acceptable dosage form, which are administered in certain doses, applied or mixed appropriately. Pharmaceutical formulations may include:

a) potential formulations—filler, in particular, pyrogen-free water, buffer or normal saline solution;

b) ointments, creams, aerosols—media, in particular vegetable or synthetic oil, lanolin, petrolatum, or high-molecular alcohols;

c) tablets or capsules—thinners, in particular lactose, binders, lubricating substances (e.g., stearic acid), as well as decomposition products (e.g., corn starch).

All pharmaceutical formulations under the present invention can be combined with antibacterial (e.g., antibiotics), antiviral, antitumor, immunomodulatory and other agents if, when combined, they provide a synergistic effect with the claimed pharmaceutical compositions, or are indifferent toward them, but in combination they expand a therapeutic spectrum.

Moreover, according to this invention, ABA can be used as a non-medicated agent (BAA, food additive, feed additive, personal care product component such as lotions, toothpaste, chewing gum, etc.) subject to observance of certain conditions. Such conditions include, for example, the use in compositions of those components only and only in the concentrations specified in the Codex Alimentarius.

Non-medicinal preparations based on a complex compound of the present invention have immunomodulatory effects and may be used for the prevention of infectious diseases, such as seasonal influenza, ARVI, iodine deficiency, as well as an adaptogen.

This invention is based on a surprising fact that in solutions of salts of alkali and alkaline earth metals, at a certain ionic strength in the presence of carbohydrate and/or protein, the complex is released into a solid phase in the process of iodine intercalation.

Another surprising fact, laid in the basis of this invention is that, as is established by experimental data, the present invention enables to introduce proteins in the antimicrobial agent composition that contain sites with specific immunological function.

BRIEF DESCRIPTION OF DRAWINGS

Some embodiments of the disclosure may be understood by referring, in part, to the present disclosure and the accompanying drawings, wherein.

DETAILED DESCRIPTION

Figure 1A:
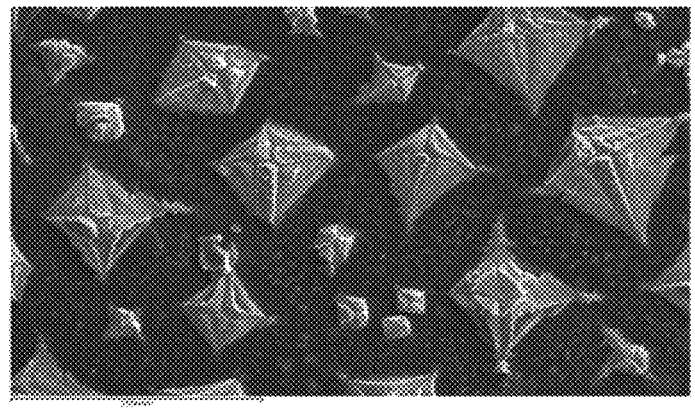
FIG. 1A represents a micrograph of a different crystal structure for the preparation of FS-1 according to a specific example embodiment of the disclosure.
Figure 1B:
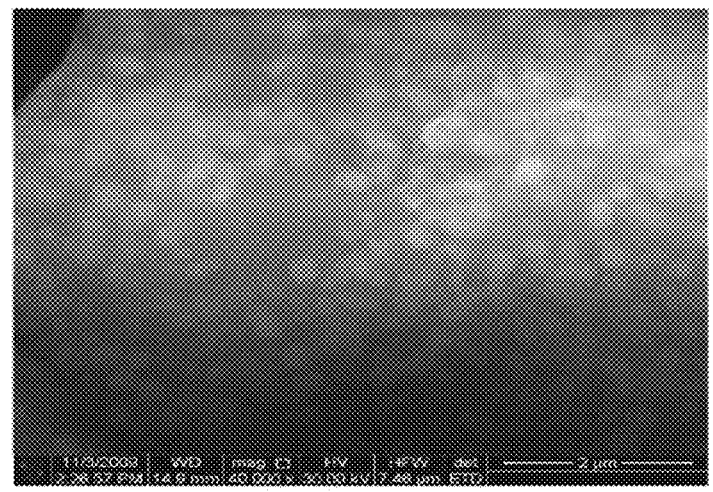
FIG. 1B represents a micrograph of different crystal structures for the preparation of FS-1 according to a specific example embodiment of the disclosure.
Figure 2A:
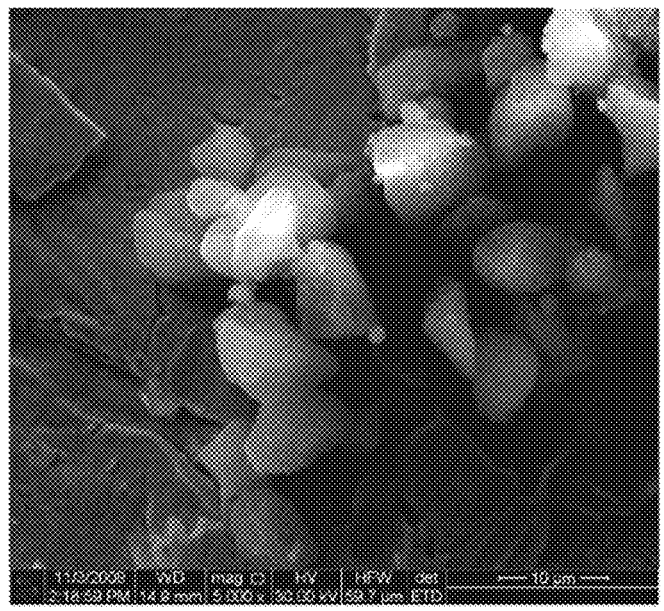
FIG. 2A represents a micrograph of different crystal structures for the preparation of FS-1 according to a specific example embodiment of the disclosure.
Figure 2B:
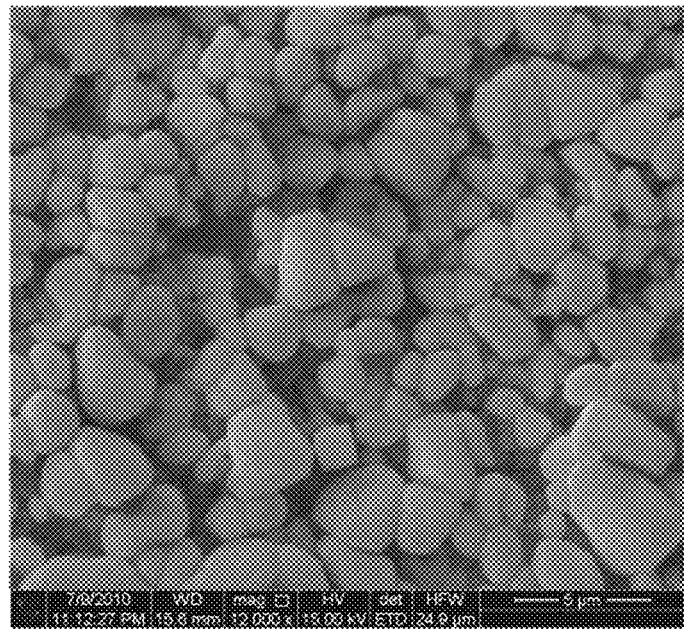
FIG. 2B represents a micrograph of different crystal structures for the preparation of FS-1 according to a specific example embodiment of the disclosure.
Figure 3:
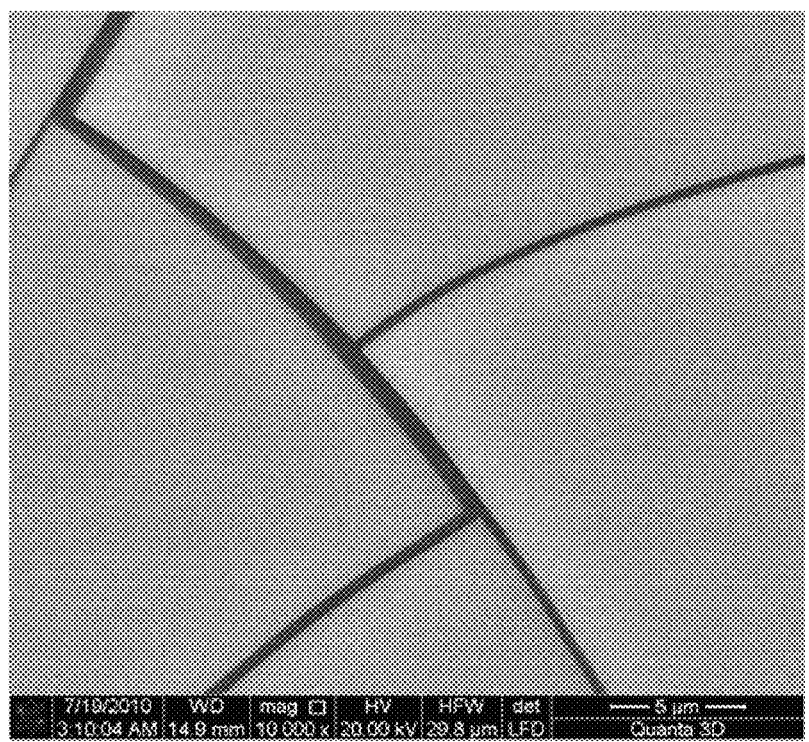
FIG. 3 represents a micrograph of different crystal structures for the preparation of FS-1 according to a specific example embodiment of the disclosure.

Proceeding from the above, in accordance with the disclosure, a method for preparation, in order to ensure the preservation of properties of immunogenic proteins in the antibacterial agent composition, is supplemented with the third and fourth stages of complex formation.

In the context of the present invention, the components, their interrelationship, and the ionic strength interval are essential features in the ABA synthesis.

Every attribute that determines the ABA composition and structure, are necessary and sufficient to achieve the formulated goal. None of them can be excluded or replaced by another one, otherwise the technical result will not be obtained. Selection of both the qualitative composition of substances that form ABA, and quantitative ratios of components, and the ionic strength interval, was based on regularities of complex formation and numerous experimental data on the determination of ABA antibacterial activity, depending on the composition of its constituent components.

The qualitative composition of substances was chosen on the basis of their biological significance and chemical properties that provide an antibacterial effect.

Carbohydrates, selected by the authors of the present invention as ligands, are an extremely important class of natural compounds. In biology and medicine, the value of carbohydrates consists in the dominant role assigned to them in animal organisms, and the complexity of their functions. Carbohydrates are involved in most biochemical processes in the form of high-molecular particles, although many bilogic fluids contain mono- and oligosaccharides (Compressive Organic Chemistry/Edited by E. Haslam. V. 5. Biological Compounds Pergamon Press, 19).

The main feature of the ABA, which represents a complex compound of iodine with carbohydrates and/or proteins and metal salts is the presence of proteins with a specific set of electron-donating functional groups in terminal amino acids and sites.

Proteins play a key role in almost all biological processes; determine the course of biological reactions in cells and are involved in a variety of other functions—such as transport of substances and their accumulation.

The present invention also includes low-molecular peptides and their constituent monomers.

Transport role of proteins is extremely important, because a diffusing molecule bound with protein, in case of passing through the membrane, is not chemically modified and does not link with other types of molecules. Mediated, or simplified, membrane transport processes are characterized by saturation kinetics (i.e. the transport system can be saturated by the transported solute) and specificity to transported substance.

The possibility of mediated transport is due to proteins that can reversibly bind specific substrates, including iodine molecule. These transporting protein molecules have different names: transport systems, transporters, carriers, or translocases.

Table 1 shows the ABA compositions, synthesized from carbohydrates, proteins, and iodine at different ionic strengths of the solution created by the salts of alkali and alkaline earth metals. The crystalline structure of some compounds (antibacterial agent), depending on the ratio of carbohydrate:protein (polypeptide), is shown on optical and electronic photographs, FIG. 1-4.

Figure 4:
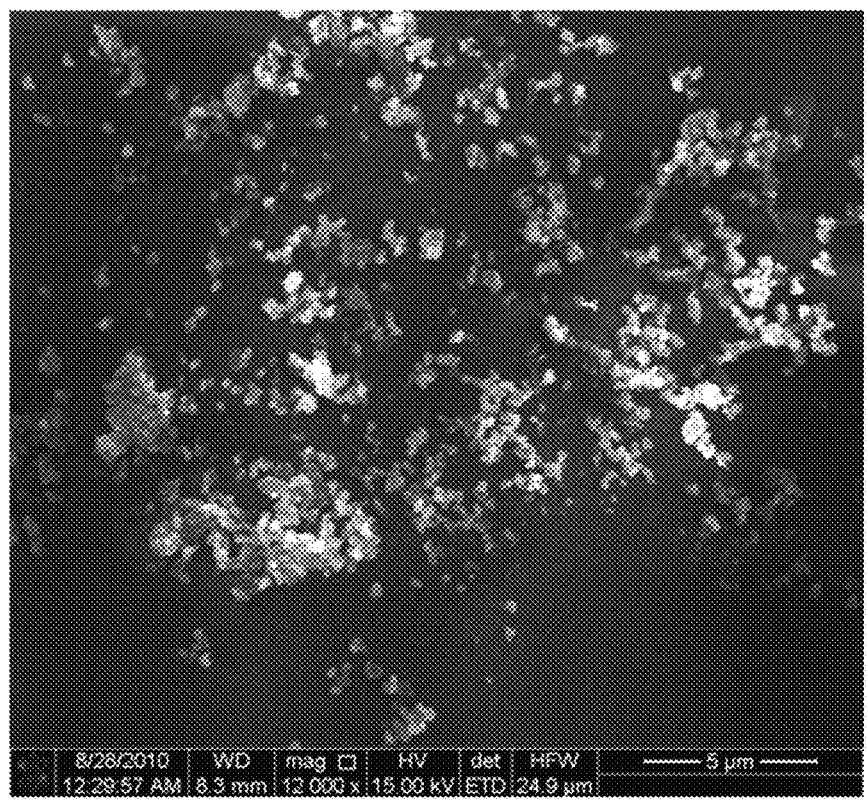
FIG. 4 represents a micrograph of different crystal structures for the preparation of FS-1 according to a specific example embodiment of the disclosure.

As can be seen in the photographs, ABA can form nanocrystals (FIG. 1: 1A with 400× enlargement, 1B with 40000× enlargement), microcrystals (FIG. 2: 2A with 5000× enlargement, 2B with 12000× enlargement) that are rather large (0.1 mm), monocrystals (FIG. 3), or crystals of various sizes (FIG. 4).

The size of crystals decreases with increasing content of carbohydrate relative to protein (polypeptide), all other things being equal (ionic strength of the solution), as well as with increasing the ratio of iodine:carbohydrate, and/or protein (peptide).

The reaction of ABA synthesis, according to the method claimed, proceeds consistently by complexation reactions. At the first stage, a formation of complexes between carbohydrates ($L_1$), protein ($L_2$), polymers ($L_3$), and salts containing calcium and magnesium cations, takes place.

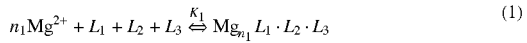

(1)

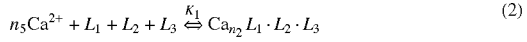

(2)

In the solution, prepared for iodine intercalation, the complexation of iodine and potassium iodide takes place:

(3)

There is an intercalation of iodine and/or polyiodide ion taking place in compounding of the above solutions, i.e. interaction between the complex particles formed both in the first solution and in the second one. In this process a redistribution of substances that make up ABA (complex) according to their donor-acceptor properties, occurs.

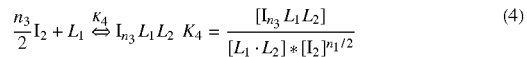

(4)

Triiodide ion produced as a result of reaction (3) is also a strong complexing agent, just as a molecular iodine.

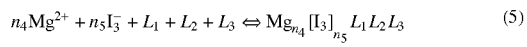

(5)

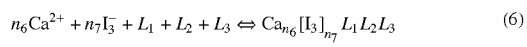

(6)

ABA Output:

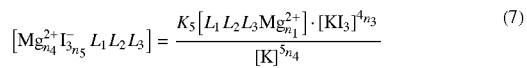

(7)

$$\left[Ca_{n_4}^{2+}I_{3_{n_7}}^-L_1L_2L_3\right] = \frac{K_6[L_1L_2L_3Ca_{n_5}]\cdot[KI_3]^{5n_4}}{[K]^{6n_5}}$$ (8)

The final product output depends on physico-chemical parameters of the reaction (Table 2, 3).

The unexpected fact was that at a certain ionic strength of the reaction medium, the ABA output approaches 100%.

Figure 5:
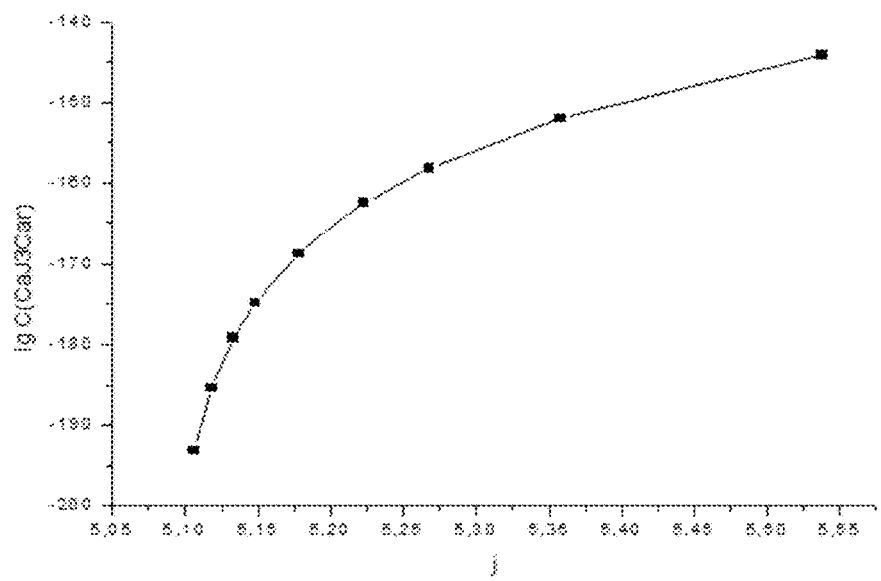
FIG. 5 shows the dependence of the yield for calcium complex of triiodide-ion with carbohydrate on the ionic strength according to a specific example embodiment of the disclosure.
Figure 6:
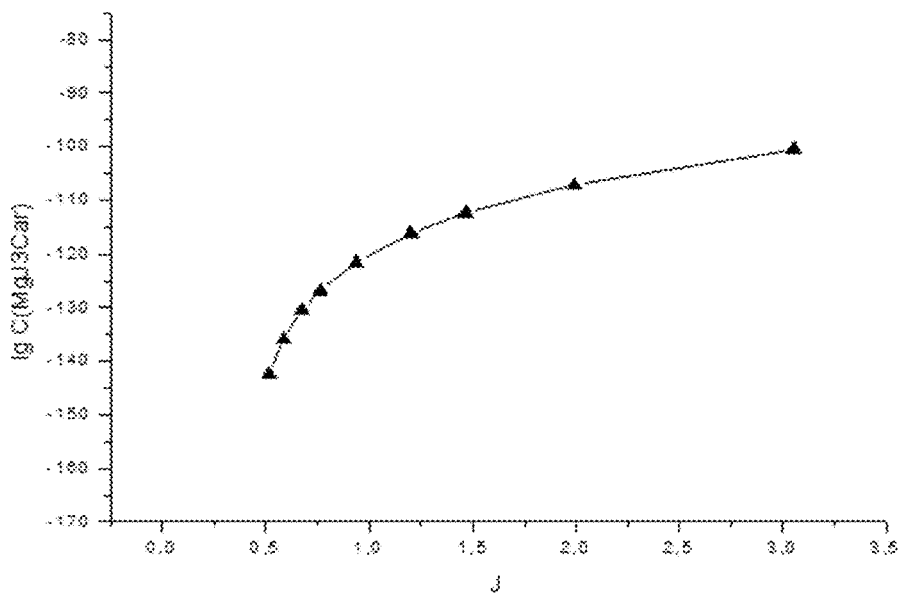
FIG. 6 shows the dependence of the yield for the magnesium complex of triiodide ion with carbohydrates on the ionic strength according to a specific example embodiment of the disclosure.

According to results of calculation of assumed equilibrium, the ABA output changes (increases) with the increase in ionic strength (FIG. 5, 6). There is an especially significant effect of ionic strength observed for the complex containing magnesium ions (FIG. 6), which may be due to characteristics of this ion as a harder acid according to Pearson [Pearson R. G., Journal ACS, 1963, 85, cl. 3533. Pearson R. G. Journal Chemical Education, 1968, 45, cl. 643. Pearson R. G, Chemical Communication, 1968, cl. 65, Gehlen H. Z., Physical chemistry, 1954, 203, 125. Finston H. Z., Rychtman A. C., A new view of current acid-base series. N.Y., Wile, 1982].

Figure 7:
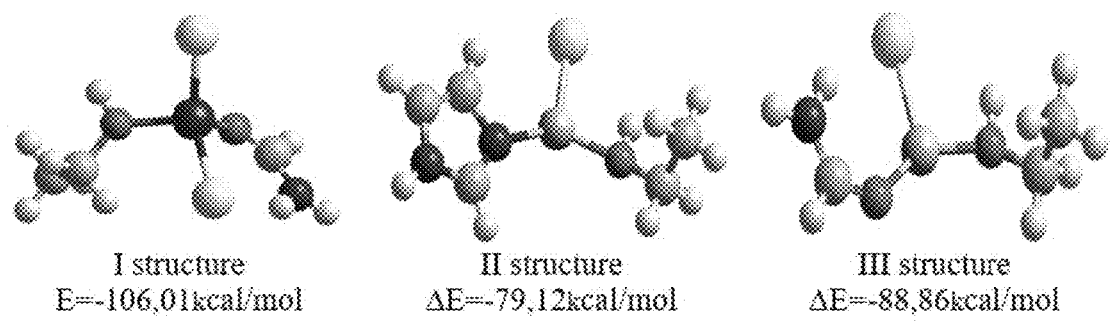
FIG. 7 shows the formation of stable coordination compounds in the system carbohydrate-protein-salts LiCl, MgCl according to a specific example embodiment of the disclosure.

Even more surprising was the fact of ABA crystals formation, which represents an ionic polymer complex, in the process of extraction using the method of centrifugal chromatography and/or drying; at that the composition of monocrystals is well-defined and constant, which indicates the formation of an individual ABA compound. The ABA structure and sequence of actions for this structure formation, according to method for antibacterial agent preparation claimed after this invention, can be represented as follows (FIG. 7). In this figure, blue balls are carbon atoms, dark blue—nitrogen atoms, yellow—chlorine atoms, red—oxygen atoms, black—magnesium atoms, brown—lithium atoms. For the structure I ΔE=−106.01 kcal/mol; for the structure II ΔE=−79.12 kcal/mol, and for the structure III ΔE=−88.86 kcal/mol.

Formation of complex polyionic compounds in the carbohydrate-protein-salt system of alkali or alkaline earth metal is confirmed through quantum-chemical calculations and UV, Fourier-transform IR spectroscopy, electron and optical microscopy, quantum-chemical calculations data.

Within the framework of initio quantum-chemical 3-21G** method, calculation of I-III structures was performed (FIG. 7). In calculations the carbohydrate was simulated with ethanol, protein skeleton—with amide, and one of the most donor-active acid residues, histidine,—with imidozol. ΔE complexation energy was calculated as follows:

$$\Delta E = E(\text{compl}) - (E(\text{LiCl}) + E(\text{ethanol}) + E(\text{amid or imidazol})$$

For the structure I ΔE=−106.01 kcal/mol; for the structure II ΔE=−79.12 kcal/mol; for the structure III ΔE=−88.86 kcal/mol. Calculations have shown that coordination of salts LiCl, $MgCl_2$ with donor-active groups of protein and carbohydrate is energetically favorable.

In intercalation of molecular iodine into the system, the complexes IV-VII are formed, in which molecular iodine is coordinated by the protein and lithium halongenides, and lithium halogenides are coordinated by carbohydrate.

Figure 8:
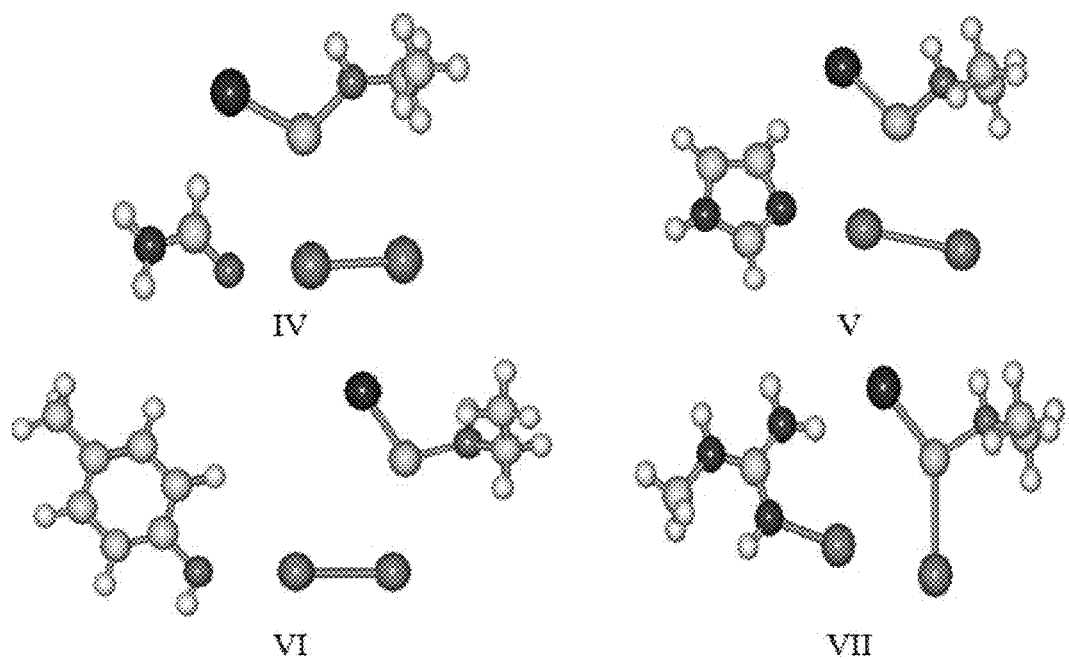
FIG. 8 shows the structures illustrating the interaction of molecular iodine with lithium halides, carbohydrates, and side amino acid residues of the protein according to a specific example embodiment of the disclosure.

Stabilities calculation of the complexes of molecular iodine with lithium halogenides, carbohydrates, and lateral amino acid residues of proteins suggests that in the process of molecular iodine intercalation in the system there are complexes formed (IV-VII FIG. 8), in which molecular iodine is coordinated by the protein, and lithium halongenides and lithium halogenides are coordinated by carbohydrate.

Table 4 shows the coordination bond lengths and AE for stabilization energy of complexes.

ΔE are calculated as follows:

$$\Delta E = E_1(\text{compl.}) - (E_2 + E_3), \quad (9)$$

where $E_1$ is total complex energy, $E_2$—is total $LiClOHC_2H_5$ energy;

$E_3$—total energy of $I_2$ complex with amino-acid residue.

As can be seen from Table 4, the most stable complex is formed with participation of arginine (structure VII), in this case I—I bond breaks; in such a complex the properties of molecular iodine are not preserved. Comparison of the stabilization energies for complexes of molecular iodine with arginine (−18.17 kJ/mol), and with adenosine (−10.93 kcal/mol) and guanine (−11, 50 kJ/mol), suggests that if arginine is included in the ABA composition, $I_2$ molecule remains in the structure of the formulation and will not form a complex with DNA nucleotides.

In I-III complexes I—I bond does not break, but is weakened only. After arginine the most stable complexes are obtained with participation of carbonyl group of protein amide fragment. Amide fragment is a part of polypeptide skeleton and is a part of amino-acid residue of asparagine and glutamine.

The output of final product depends on physico-chemical parameters of the reaction—K. . . stoichiometric coefficient n, and concentration of reagents.

Figure 9:
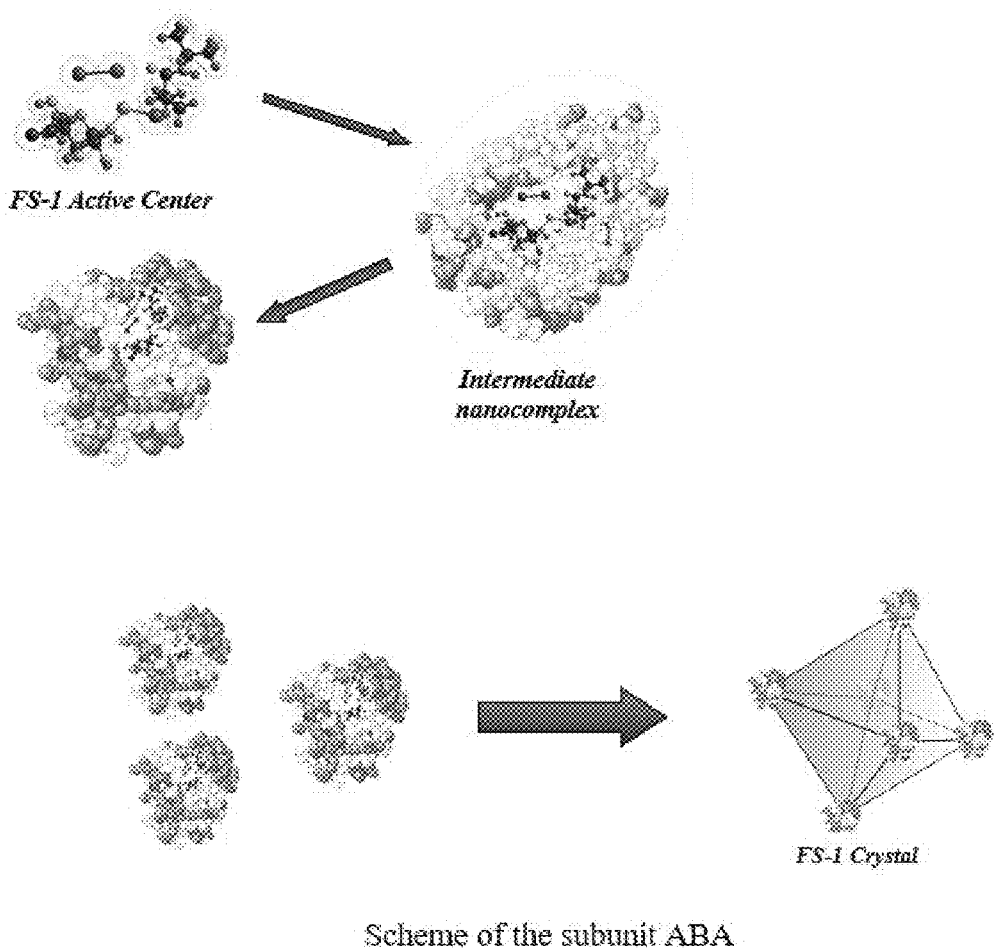
FIG. 9 represents a diagram of the ABA subunit formation according to a specific example embodiment of the disclosure.

Based on the data of UV, Fourier transform IR spectroscopy, electron and optical microscopy, quantum-chemical calculations, the structure of ABA and sequence of acts in formation of this structure, according to the method for ABA preparation claimed in the present invention, schematically can be represented as follows (FIG. 9).

Formation of ABA subunit (molecule) occurs after the influence of ionic strength in the range from 0.015 and up to 10.2, corresponding to the pressure of 286-2860 kg/cm². After the influence of such pressure (ionic strength), carbohydrate and protein macromolecules are packed in such a way that terminal amino acid triplets not involved in complexation are oriented outwards from the core protein and/or polypeptide skeletal chain, and perform anchoring of antibacterial agent on the cell membrane through chain-terminal amino acids, containing electron-donor functional groups, which is directly evident from the data on ABA immunothropic action, given below.

A method for the claimed ABA preparation is the following:

A carbohydrate sample is dissolved in an appropriate solvent such as water, dioxane and other. In this solution, in order to obtain complex compounds certain samples of metal salts and sodium chloride are added to generate the appropriate ionic strength of the solution (Product A).

A protein sample is dissolved in an appropriate solvent such as water, dioxane and other. In this solution, to obtain complex compounds certain samples of metal salts and sodium chloride are added to generate the appropriate ionic strength of solution (Product B).

A sample of crystalline iodine or iodine and potassium iodide is dissolved in an appropriate solvent such as chloroform, hexane and others, and the solution stirred until complete iodine dissolving (Product C).

Then to the mixture of Products A and B, 70% of Product C is added in portions while stirring. After stirring the reaction mixture for 1 hour at 42÷43° C., a protein with specific immunothropic functions containing at least one terminal amino acid with electron-donor functional groups is added to the solution, and a final 30% iodine intercalation is conducted by adding in portions the remaining 30% of Product C. The resulting antibacterial agent (ABA) (a complex compound of iodine with carbohydrates and/or proteins and metal salts), is extracted using a suitable method, and dried. A drug based on this antibacterial agent was prepared using the known methods, in a form of a solution for oral administration, solution for parenteral use, tablets and capsules.

Analysis of the antibacterial agent was performed by color-indication, potentiometric titration (Sartorius Professional Meter PP-50), capillary electrophoresis (Agilent Technologies CE3D, USA), vibrational (IK) spectroscopy with Fourier transform (Thermo Electron Corporation Nicolet 6700), electron spectroscopy in ultraviolet and visible spectrum (PerkinElmer Lambda 35).

Microscopy of complex compounds was performed in a scanning electron microscope Quanta 200i 3D (FEI Company, USA).

The product cytotoxicity was determined in vitro by microscopy and using MTT-test in monolayer subinoculated cell cultures RD, MDCK, MRC-5, suspension cultures of MT-2 and H9 by micromethod in 96-well plates, incubated in an atmosphere containing 5% $CO_2$ at 37° C. (Table 5).

Determination of ABA minimum inhibitory concentration (MIC) against clinical isolates of MRSA and MSSA, and reference strains of *Staphylococcus aureus* ATCC 43300 and *Staphylococcus aureus* ATCC 29213 was conducted by serial dilution method in culture medium [Clinical Laboratory Standards Institute, *Document M7-A7. Methods for dilution antimicrobial susceptibility tests for bacteria that grow aerobically; Approved standard*-7 th Edition, Wayne, Pa.: Clinical Laboratory Standards Institute, 2006] (Table 6).

Studies of ABA synergistic action with antibiotics against clinical isolates of MRSA and MSSA, and reference strains of *Staphylococcus aureus* ATCC 43300 and *Staphylococcus aureus* ATCC 29213 were conducted by Checkerboard method [Eliopoulos G and Moellering R. *Antimicrobial* combinations. In *Antibiotics in Laboratory Medicine*, 1996, 4rd edn (Lorian, V, Ed.), Pcl. 331-396. Williams and Wilkins Co., Baltimore, Md., USA].

Determination of synergy by Time-Kill method was conducted in relation to control strain of MRSA ATCC 43300 [National Committee for Clinical Laboratory Standards, *Document M26-A. Methods for Determining Bactericidal Activity of Antimicrobial Agents; Approved Guideline* Wayne, Pa.: National Committee for Clinical Laboratory Standards, 1999].

Antimycobacterial effect of ABA FS-1 was studied based on growth dynamics of mycobacterial strains of *M. tuberculosis* H37Rv, *M. tuberculosis* MS-115 and *M. bovis Bovinus* in enriched liquid medium Middlebrook 7H9 in the presence of different concentrations of the product, compared with the growth of these strains on a medium containing no drugs, and on a medium containing the first-line agent isoniazid at concentration of 0.1 μg/ml. The studies were conducted in triplicates. Growth detection was carried out using an automated growth record system for cultures BACTEC™ MGIT 960 (Becton Dickenson, USA) in special MGIT tubes. Growth detection of mycobacterial cultures was performed every hour using Epicenter software (Becton Dickenson, USA).

To study antituberculous effect of the product made from ABA in Example 5 (FS-1) an aerogenic infection model was used in female albino guinea pigs. Inoculation was performed in aerosol chamber "GlasCol" with a dose of 150 CFU of *M. tuberculosis* H37Rv per a lung.

To study antituberculous effect of FS-1 the Dunkin Hartley line guinea pigs were used. The inoculation was carried out intramuscularly on the basis of 0.5 ml of suspension containing ≈307-692 of *M. tuberculosis* $H_{37}R_v$ bacterial bodies in 1 ml per animal.

Determination of ABA antiviral action in vitro against influenza virus A/FPV/Waybrige/78/H7N7 and herpes simplex virus, strain "Victory", was performed using micromethod on subinoculated MDCK and RD cell cultures. Substances were added in concentrations equal to ½, ¼, ⅛, 1/16 of the maximum tolerated concentration (MTC).

The study of FS-1 antiviral action against human immunodeficiency virus HIV-1 (LAI) was conducted in cell culture MT-2 (human T-lymphoblastoid cells transformed with HTLV-1 virus), with azidothymidine as the reference substance.

The source of virus-containing material was a culture fluid of N9/HTLV-IIIB line cells, chronically infected with human immunodeficiency virus HIV-1 strain (LAI).

Evaluation of FS-1 mutagenic activity in the Ames test was carried out in 4 mutagenic (auxotrophic for histidine) strains of *Salmonella thyphymurium*: TA 98, TA 100, TA 102, and TA 1535 with metabolic activation and without metabolic activation.

The study of DNA-damaging activity of FS-1 in the comet assay was performed in vitro in the mouse lymphoma cell line L5178Y and human hepatoma cell line HepG2.

The study of ABA cytogenetic activity was performed by taking account of chromosome aberrations in bone marrow leukocytes of mammals in vivo in mice.

The study of ABA cytogenetic activity was performed using micronucleus test in polychromatic and orthochromatic erythrocytes of mice's bone marrow cells in vivo.

The study of dominant lethal mutations in spermatozoa in mammals when administered FS-1 was performed in vivo in mice.

Most of the examples given in the invention description that illustrate the ABA effectiveness against pathogenic microorganisms, including museum and clinical isolates of multidrug-resistant (MDR) *Mycobacterium tuberculosis* belong to the ABA-based drug after Example 5 (FS-1), without being limited to them.

Experiments for studying radioprotective properties of the drug ABA FS-1 were conducted in white rats weighing 190-200 g and white mice weighing 22-25 g. In irradiation experiments the animals were exposed to single uniform radiation in RUM-17 therapeutic x-ray apparatus (180 kV, 10 mA, filters 0.5 mm Cu+1.0 Al, focal distance—40 cm, radiation dose rate—178 R./min) in doses of 800 R (radiation doses close to LD50).

Induction of myelosuppression with ABA FS-1 was performed by the method of [Galoyan A. A., Korochkin L. I., Rybalkina E. J., Pavlova GV., Saburina I. N., Zaraiski E. I., Galoyan N. A., Davtyan T. K., Bezirganyan K. B., Revishchin A. V. Hypothalamic proline-rich polypeptide enhances bone marrow colony-forming cell proliferation and stromal progenitor cell differentiation//Cell Transplantation. —2008. —Vol. 17. —P. 1061-1066].

Sampling of peripheral blood and bone marrow of animals was carried out by the method of [Bezirganyan K B, Davtyan T K, Galoyan A A Hypothalamic proline rich polypeptide regulates hematopoiesis//Neurochem. Res.—2010.—Vol. 35.—CL. 917-924. Gershanovich M. L., Paikin M. D. Symptomatic treatment of malignancies. $2^{nd}$ ed.—Moscow: Medicine, 1986. —285p.].

Assessment of myelosuppression was performed by counting the absolute and relative content of leukocytes, lymphocytes and monocytes in peripheral blood using an automated hematology analyzer Celly v 2.20, Hycel Diagnostics.

The recovery of bone marrow hematopoietic function was estimated using clonogenic test. [Bezirganyan K. B., Davtyan T. K., Galoyan A. A. Hypothalamic proline rich polypeptide regulates hematopoiesis//Neurochem. Res.—2010.—Vol. 35.—CL. 917-924], by determining the number of granulocyte-monocyte colony-forming (CFU-GM) progenitor bone marrow cells. For this purpose, bone marrow cells were cultured in a medium Methocult™ GF R3774, containing methylcellulose and growth factors, progenitor cells (stem cell factor, GM-CSF and IL-3), StemCell Technologies Inc (cat N° 03774).

Example No. 1 FS-1.1

ABS synthesis is conducted in the laboratory reactor D-55122 Mainz, type RührgefäB 2L, QVF ENGINEERING GMBH, after the constant stirring. Temperature is maintained using thermostat "HUBER"—Ministat 230 CC2. 130 g of carbohydrate is dissolved in 500 ml of water at 50° C. Further, 3.0 g of sodium chloride and 1.98 mg of calcium chloride dissolved in 100 ml of water are added. The mixture is thoroughly stirred and cooled to 43° C. (Product A).

5.0 g of albumin are dissolved in 150 ml of water and then 3.96 g of lithium chloride, 8.4 g magnesium chloride and 2.0 g of sodium chloride added (Product B). 135 ml of the resulting solution is poured in the reactor. Reactor mixture is agitated for 20 minutes, and after that the solution temperature reduced to 25° C.

0.82 g of $I_2$ and H 1.2 g of potassium iodide are dissolved in 100 ml of water (Product B). 70 ml of the resulting solution is poured in portions in the reactor. Iodine intercalation is performed for 2 hours at 25° C., and after that the rest 15 ml of Product B are added. After 1 hour, another 30 ml of Product B is added in portions into reactor, and iodine intercalation is completed within 2 hours.

Ionic strength of the solution is 13.6.

Figure 10A:
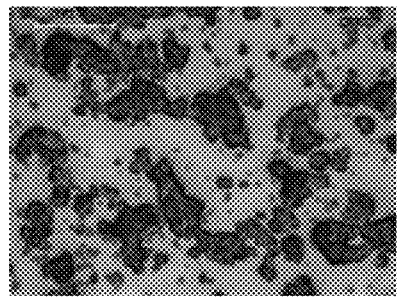
FIG. 10A represents a micrographs of the compound by example 1 according to a specific example embodiment of the disclosure.
Figure 10B:
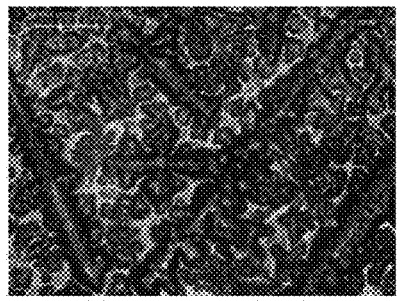
FIG. 10B represents a micrographs of the compound by example 2 according to a specific example embodiment of the disclosure.
Figure 10C:
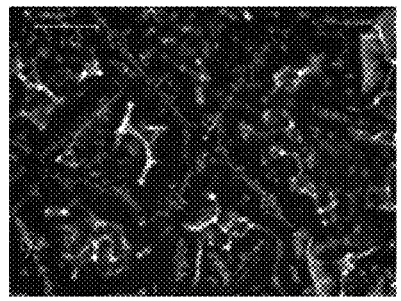
FIG. 10C represents a micrographs of the compound by example 3 according to a specific example embodiment of the disclosure.
Figure 10D:
FIG. 10D represents a micrographs of the compound by example 4 according to a specific example embodiment of the disclosure.

The resulting ionic nanostructured ABS complex is extracted from the reaction medium using a suitable method, for example, centrifugal chromatography method in "Kromaton" FCPC (Fast Centrifugal Chromatography), and dried (FIG. 10(a)).

Analysis Results:

|  | Dextrin | Albumin | PVA | LiCl | NaCl | MgCl$_2$ | CaCl$_2$ | I$_2$ | KI |
|---|---|---|---|---|---|---|---|---|---|
| Mole fractions, % | 0.40 | 0.59 | 63.58 | 0.02 | 0.01 | 11.62 | 10.62 | 2.21 | 10.95 |

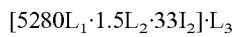

$[5280L_1 \cdot 1.5L_2 \cdot 33I_2] \cdot L_3$

Example No. 2 FS-1.2

ABS synthesis is conducted in the laboratory reactor D-55122 Mainz, type RührgefäB 2L, QVF ENGINEERING GMBH, after the constant stirring. 108.3 g of dextran is dissolved in 500 ml of water at 45° C. Temperature is maintained using a thermostat "HUBER"-Ministat 230 CC2. Further, 2.5 g of PVA dissolved in 150 ml of water, 4.0 g of sodium chloride and 1.65 g of calcium chloride dissolved in 100 ml of water, are added. The mixture is thoroughly stirred and cooled to 43° C. (Product A).

4.17 g of albumin is dissolved in 150 ml of water, and then 3.3 g of lithium chloride, 7.0 g of magnesium chloride and 0.17 g of sodium chloride are added. The resulting solution is transferred to the reactor when the temperature of Product A specified above is reached. The mixture is stirred for 20 minutes, and after that the temperature of reaction zone is reduced to 25° C. (Product B).

2.0 g of I$_2$ and 3.0 g of potassium iodide are dissolved in 100 ml of water. The resulting solution is poured in portions into the complex compound solution (Product B). Iodine intercalation is performed for 4 hours at 25° C.

Ionic strength of the solution is 13.2.

The resulting ionic nanostructured ABA complex is extracted from the reaction medium using a suitable method, and dried (FIG. 10 (b)).

Analysis Results:

|  | Dextrin | Albumin | PVA | LiCl | NaCl | MgCl$_2$ | CaCl$_2$ | I$_2$ | KI |
|---|---|---|---|---|---|---|---|---|---|
| Mole fractions, % | 62.35 | 0.02 | 0.01 | 11.40 | 10.40 | 10.74 | 2.2 | 1.15 | 1.73 |

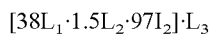

$[38L_1 \cdot 1.5L_2 \cdot 97I_2] \cdot L_3$

Example No. 3 FS-1.3

ABS synthesis is conducted in the laboratory reactor D-55122 Mainz, type RührgefäB 2L, QVF ENGINEERING GMBH, after the constant stirring. 72.0 g of carbohydrate is hydrolyzed in 600 ml of water at 60° C. Temperature is maintained using a thermostat "HUBER"—Ministat 230 CC2. Further, 1.7 g of PVA dissolved in 100 ml of water, 2.8 g of sodium chloride and 1.1 g of calcium chloride dissolved in 100 ml of water are poured in. The mixture is thoroughly stirred and cooled to 43° C. (Product A).

2.8 g of albumin is dissolved in 150 ml of water, and then 2.2 g of lithium chloride, 4.66 g of magnesium chloride and 0.8 g of sodium chloride are added. The resulting solution is transferred to the reactor when the temperature of Product A specified above is reached. The mixture is stirred for 20 minutes, and after that the temperature in reaction zone is reduced to 25° C. (Product B).

Ionic strength of the solution is 10.8

4.1 g of I$_2$ and 6.0 g of potassium iodide are dissolved in 100 ml of water. The resulting solution is poured in portions into the complex compound solution (Product B). Iodine intercalation is performed for 4 hours at 25° C.

The resulting ionic nanostructured ABA complex is extracted from the reaction medium using a suitable method, and dried (FIG. 10) (c)).

Analysis Results:

|  | Dextrin | Albumin | PVA | LiCl | NaCl | MgCl$_2$ | CaCl$_2$ | I$_2$ | KI |
|---|---|---|---|---|---|---|---|---|---|
| Mole fractions, % | 0.96 | 0.04 | 0.03 | 24.38 | 22.46 | 22.95 | 4.65 | 7.57 | 16.96 |

$[611L_1 \cdot 24L_2 \cdot 294I_2] \cdot L_3$

Example No. 4 FS-1.4

ABS synthesis is conducted in the laboratory reactor D-55122 Mainz, type RührgefäB 2L, QVF ENGINEERING GMBH, after the constant stirring. 72.0 g of carbohydrate is hydrolyzed in 550 ml at 100° C. Temperature is maintained using a thermostat "HUBER"-Ministat 230 CC2. Further, 1.7 g of PVA dissolved in 250 ml of water is poured in (Product A). The mixture is thoroughly stirred during 20 min, after that the temperature in reaction zone is reduced to 25° C.

4.1 g of I$_2$ and 6.0 g of potassium iodide are dissolved in 200 ml of water. The resulting solution is poured in portions into the complex compound solution (Product B). Iodine intercalation is performed for 4 hours at 25° C.

The resulting ionic nanostructured ABA complex is extracted from the reaction medium using a suitable method, and dried (FIG. 10 (d)).

Ionic strength of the solution is 3.02.

Analysis Results:

|  | Carbohydrate | PVA | $I_2$ | KI |
|---|---|---|---|---|
| Mole fractions, % | 29.67 | 66.45 | 3.78 | 0.10 |

$[37L_1 \cdot 294I_2] \cdot L_3$

Example No. 5 FS-1

ABS synthesis is conducted in the laboratory reactor D-55122 Mainz, type Rührgefäß 2L, QVF ENGINEERING GMBH, after the constant stirring. 130 g of mixture of amylase and amylopectin in the ratio of 1:4 is dissolved in 500 ml of water at 43° C. Temperature is maintained using a thermostat "HUBER"—Ministat 230 CC2. Further, 3.0 g of PVA dissolved in 150 ml of water, 4.5 g of sodium chloride, and 2.0 g of calcium chloride dissolved in 100 ml of water are poured in (Product A).

5.0 g of albumin is dissolved in 150 ml of water, and then 4.0 g of lithium chloride, 8.4 g of magnesium chloride and 0.5 g of sodium chloride are added. The resulting solution is transferred to the reactor. The mixture is stirred for 20 minutes, and after that the temperature of reaction zone is reduced to 25° C. (Product B).

8.2 g of $I_2$ and 12.1 g of potassium iodide are dissolved in 100 ml of water. The resulting solution is poured in portions into the complex compound solution (Product B). Intercalation of iodine is carried out in two stages, as described in the previous examples.

Figure 11:
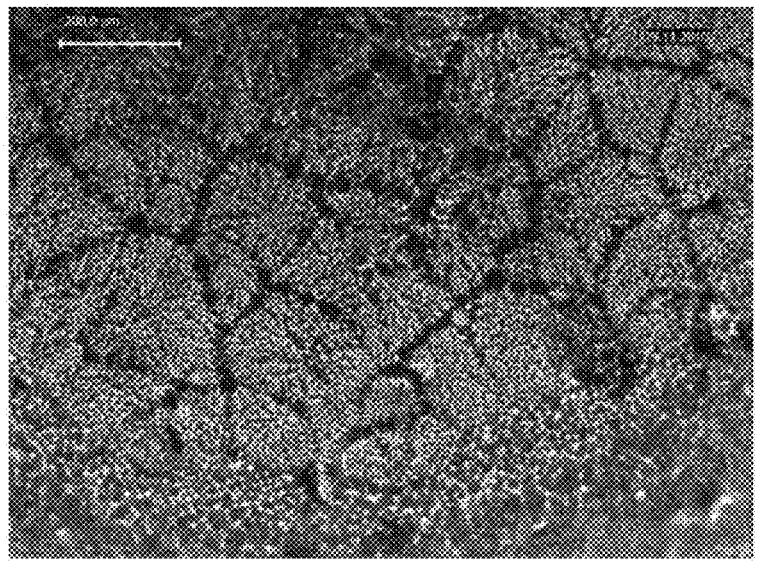
FIG. 11 represents a micrograph of the compound by Example 5 (FS-1) according to a specific example embodiment of the disclosure.

The resulting ionic nanostructured ABA complex is extracted from the reaction medium using a suitable method, and dried (FIG. 11).

Ionic strength of the solution is 20.60.
Analysis Results:

|  | Amylum | Albumin | PVA | LiCl | NaCl | $MgCl_2$ | $CaCl_2$ | $I_2$ | KI |
|---|---|---|---|---|---|---|---|---|---|
| Mole fracture, % | 0.94 | 0.04 | 0.02 | 23.90 | 21.62 | 22.31 | 4.56 | 8.17 | 18.44 |

$[38L_1 \cdot 2L_2 \cdot 333I_2] \cdot L_3$

Example No. 6 FS-1.5

ABS synthesis is conducted in the laboratory reactor D-55122 Mainz, type Rührgefäß 2L, QVF ENGINEERING GMBH, after the constant stirring. 24.1 g of carbohydrate is hydrolized in 500 ml of water at 80° C. until a certain molar weight is reached. Temperature is maintained using a thermostat "HUBER"—Ministat 230 CC2. Further, 2.8 g of PVA dissolved in 150 ml of water is poured in. The mixture is thoroughly stirred and cooled to 43° C. (Product A).

34.0 g of $I_2$ and 50.5 g of potassium iodide are dissolved in 100 ml of water. The resulting solution is poured in portions into the complex compound solution (Product C). Intercalation of iodine is carried out in two stages, during 4 hours at 25° C.

The resulting ionic nanostructured ABA complex is extracted from the reaction medium using a suitable method, and dried (FIG. 10 (d)).

Ionic strength of the solution is 25.3.
Analysis Results:

|  | Carbohydrate | PVA | $I_2$ | KI |
|---|---|---|---|---|
| Mole fractures, % | 0.16 | 0.02 | 30.50 | 69.32 |

$[8L_1 \cdot 1488I_2] \cdot L_3$

Example No. 7 FS-1.6

ABS synthesis is conducted in the laboratory reactor D-55122 Mainz, type Rührgefäß 2L, QVF ENGINEERING GMBH, after the constant stirring. 24.1 g of carbohydrate is hydrolized in 500 ml of water at 100° C. until a certain molar weight is reached. Temperature is maintained using a thermostat "HUBER"—Ministat 230 CC2. Further, 2.8 g of PVA dissolved in 150 ml of water, 0.8 g of sodium chloride, and 0.37 g of calcium chloride dissolved in 100 ml are poured in. The mixture is thoroughly stirred and cooled to 43° C. (Product A).

0.93 g of albumin is dissolved in 150 ml of water, and then 0.73 g of lithium chloride, 1.55 g of magnesium chloride and 0.13 g of sodium chloride are added. The resulting solution is transferred to the reactor after the required Product A temperature specified above is reached. The mixture is stirred for 20 minutes (Product B) and after that the temperature of reaction zone is reduced to 25° C.

34.0 g of $I_2$ and 50.5 g of potassium iodide are dissolved in 100 ml of water. The resulting solution is poured in portions in the complex compound solution (Product C). Intercalation of iodine is carried out in two stages, during 4 hours at 25° C.

Figure 10E:
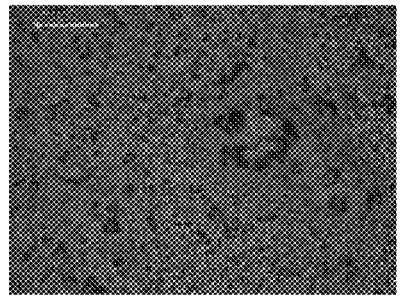
FIG. 10E represents a micrographs of the compound by example 6 according to a specific example embodiment of the disclosure.
Figure 10F:
FIG. 10F represents a micrographs of the compound by example 7 according to a specific example embodiment of the disclosure.

The resulting ionic nanostructured ABA complex is extracted from the reaction medium using a suitable method, and dried (FIG. 10(e)).

Ionic strength of the solution is 27.9.
Analysis Results:

|  | Carbohydrate | Albumin | PVA | LiCl | NaCl | $MgCl_2$ | $CaCl_2$ | $I_2$ | KI |
|---|---|---|---|---|---|---|---|---|---|
| Mole fractures, % | 0.14 | 0.006 | 0.02 | 3.51 | 3.23 | 3.31 | 0.68 | 27.23 | 61.70 |

$[26L_1 \cdot L_2 \cdot 4970I_2] \cdot 3L_3$

Example No. 8 FS-1.7

ABS synthesis is conducted in the laboratory reactor D-55122 Mainz, type Rührgefäß 2L, QVF ENGINEERING GMBH, after the constant stirring. 130.0 g of dextrin and 3.0 g 0f PVA is dissolved in 500 nil of water at 50° C. Temperature is maintained using a thermostat "HUBER"—

Ministat 230 CC2. Further, 4.0 g of sodium chloride and 2.0 g of calcium chloride dissolved in 100 nil of water are poured in. The mixture is thoroughly stirred and cooled to 43° C. (Product A).

5.0 g of albumin is dissolved in 150 ml of water, and then 4.0 g of lithium chloride, 8.4 g of magnesium chloride and 1.0 g of sodium chloride are added. The resulting solution is transferred to the reactor after the required Product A temperature specified above is reached. The mixture is stirred for 20 minutes (Product B), and after that the temperature of reaction zone is reduced to 25° C.

8.2 g of $I_2$ and 12.1 g of potassium iodide are dissolved in 100 ml of water. 70 ml of the resulting solution is poured in portions in the complex compound solution (Product B). Iodine intercalation is carried out in two stages during 4 hours at 25° C.

0.6 g of IL-2 is dissolved in 150 ml of water and slowly added to the reactor. 30 minutes after the charge of IL-2, 20 nil of Product B is added to the reactor. The resulting ionic nanostructured ABA complex is extracted from the reaction medium using a suitable method, and dried (FIG. 10(f)).

Ionic strength of the solution is 20.60.

Analytic Results:

|  | Dextrin | Albumin | IL-2 | PVA | LiCl | NaCl | MgCl$_2$ | CaCl$_2$ | I$_2$ | KI |
|---|---|---|---|---|---|---|---|---|---|---|
| Mole percent, % | 0.94 | 0.04 | 0.01 | 0.02 | 23.9 | 21.62 | 22.30 | 4.56 | 8.17 | 18.44 |

$[79L_1 \cdot 3L_2 \cdot 2.684I_2] \cdot 2L_3$

Example No. 9 FS-1.8

ABS synthesis is conducted in the laboratory reactor D-55122 Mainz, type RührgefäB 2L, QVF ENGINEERING GMBH, after the constant stirring. 13.1 g of carbohydrate is hydrolyzed in 100 ml at 130° C. Temperature is maintained using a thermostat "HUBER"-Ministat 230 CC2. Further, 3.0 g of PVA dissolved in 150 ml of water, 0.3 g of sodium chloride and 0.2 g of calcium chloride dissolved in 100 ml of water are poured in (Product A). The mixture is thoroughly stirred and cooled to 43° C. Синтез iроводят АБА в лабораторном реакторе фирмы «QVF ENGINEERING» GMBH D-55122 Mainz тип RührgefäB 2L при постоянном перемешивании.

0.51 g of albumin is dissolved in 150 ml of water, and then 0.4 g of lithium chloride, 0.84 g of magnesium chloride and 0.2 g of sodium chloride are added. The resulting solution is transferred to the reactor after the required Product A temperature specified above is reached. The mixture is stirred for 20 minutes (Product B), and after that the temperature in reaction zone is reduced to 25° C.

74.5 g of $I_2$ and 110.0 g of potassium iodide are dissolved in 500 ml of water. The resulting solution is poured in portions in the complex compound solution (Product B). Intercalation of iodine is carried out in two stages, during 4 hours at 25° C.

Figure 10G:
FIG. 10G represents a micrographs of the compound by example 8 according to a specific example embodiment of the disclosure.
Figure 10H:
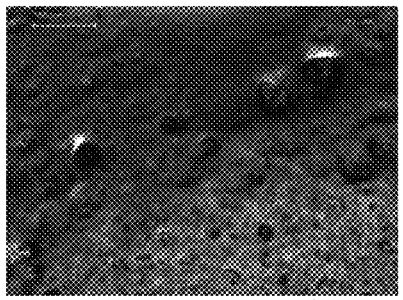
FIG. 10H represents a micrographs of the compound by example 9 according to a specific example embodiment of the disclosure.

The resulting ionic nanostructured ABA complex is extracted from the reaction medium using a suitable method, and dried (FIG. 10(g)).

Ionic strength of the solution is 56.3.

Analysis Results:

|  | Carbohydrate | Albumin | PVA | LiCl | NaCl | MgCl$_2$ | CaCl$_2$ | I$_2$ | KI |
|---|---|---|---|---|---|---|---|---|---|
| Mole fractures, % | 0.04 | 0.002 | 0.01 | 0.96 | 0.87 | 0.9 | 0.18 | 29.8 | 67.31 |

$[25L_1 \cdot L_2 \cdot 0.19575I_2] \cdot 7L_3$

In biological activity testing it was established that ABA FS-1 is active in vitro both against clinical isolates, and control strains of MRSA and MSSA. MIC of antimicrobial agent was varied from 0.938 mg/ml to 0.234 mg/ml.

Tests for synergy with oxacillin have shown a decrease in MIC of both drugs. The decline was from 256 to 64 μg/ml for oxacillin, and from 0.234 to 0.117 μg/ml for ALA FS-1. FTC index for this test was 0.75, which can be regarded as a partial synergy between the tested drugs.

Test for synergy with cefamandole has shown a decrease in MIC of both drugs. The reduction ranged from 64 to 8 μg/ml for cefamandole, and from 0.469 μg/ml to 0.234 μg/ml for ABA FS-1. FIC index for this test was 0.62, which determines the interaction of these antibiotics as a partial synergy.

Test for synergy with lincomycin has shown a decrease in MIC of both drugs. The reduction ranged from 64 μg/ml to 8 μg/ml for lincomycin, and from 0.234 mg/ml to 0.117 mg/ml for ABA FS-1. FIC index for this test was 0.625, which determines the interaction of these antibiotics as a partial synergy.

ABA in Examples 1-9 (FS-1.1-FS-1.8) has a greater or lesser bactericidal activity against pathogenic microorganisms of different classes (Table 6). The most acceptable and effective one, as follows from Table 6, with respect to *Mycobacterium tuberculosis*, is ABA in Example 5 (FS-1).

As the result of studying FS-1 antimycobacterial action against *M. tuberculosis* H37Rv, *M. tuberculosis* MS-115 with multidrug-resistance, and *M. bovis*, it was established that at the drug concentrations in dilutions of 1:12.5, 1:25 and 1:50 a complete suppression of reproduction of mycobacteria was observed throughout the entire registration period.

Bactericidal activity of FS-1 was evaluated in vitro using a microbiological method of double serial dilutions in Shkolnikova liquid medium, with subsequent passaging on Levenstein-Jensen medium. In vitro bactericidal activity of FS-1 at concentrations ranging from 1.750 to 0.0437 mg/ml in field strains of mycobacteria, drug-resistant clinical isolates and *M. tuberculosis* N37Rv has been established. Bacteriostatic effect of FS-1 is observed in concentrations from 0.0218 to 0.0109 mg/ml.

Bactericidal activity of FS-1 in vitro in concentration of 0.0437 mg/ml in combination with anti-TB drugs, Type I, with subsequent passaging on Levenstein-Jensen medium in relation to museum strain *M. tuberculosis* N37Rv and 8 multi-drug resistant strains, was evaluated. The research identified, with various concentrations of anti-TB drugs of Type I, museum sensitive and multidrug-resistant strains. The results are presented in Table 7.

As can be seen from Table 7, after the combined action of FS-1 with different concentrations of anti-TB drugs, the growth of multidrug resistant strains of *Mycobacterium tuberculosis* was not detected in experimental test tubes, i.e. strains were susceptible to all concentrations of anti-TB drugs of Type I, in comparison with the museum strain, where susceptibility was observed both with FS-1, and without it.

It has been established in vivo that administration of FS-1 to infected guinea pigs in a dose of 5 mg/kg has reduced the number of plated mycobacteria from the lungs of infected animals, compared with control group of animals. ABA FS-1 has a pronounced anti-inflammatory effect on the clinical course of experimental tuberculosis in guinea pigs, increasing airiness of lung parenchyma twofold.

It has been established in viva that the combined application of anti-TB drugs and FS-1 in a dose of 0.3 ml/kg on the $21^{st}$ day after the treatment initiation results in complete disappearance of tuberculosis changes in the organs of animals, regardless of the type of resistance of the infecting strain.

According to the results presented in Table 8, it is evident that in Group 3 there was a decrease in the number of tuberculosis lesions in lungs observed, and their complete disappearance on the 35th day after the treatment initiation. In Group 4 disappearance of tuberculosis lesions in lungs and liver was registered on the 28th day after the treatment initiation. In Group 5 disappearance of tuberculosis lesions in lungs and liver was registered on the $21^{st}$ day after the treatment initiation.

In groups of animals infected with multiresistant strain of mycobacteria resistant to anti-TB drugs, the following results have been observed: in Group 6 there was a progressive clinical course of tuberculosis infection; in Group 7 the disappearance of tuberculosis lesions in lungs and liver was registered on the $35^{th}$ day after the treatment initiation, in Group 8 a disappearance of tuberculosis lesions in lungs and liver was registered on the $21^{st}$ day after the treatment initiation.

Medicinal agent after the Example 5 (FS-1) in combination with anti-TB drugs, both in the group of animals infected with strains of *M. tuberculosis* H37Rv, and in the group infected with multiresistant strains of mycobacteria, has a therapeutic effect on the clinical course of tuberculosis. Pathological changes that are typical in tuberculosis disappear after 21 and 28 days respectively (groups 4 and 7).

Animals in the control group who did not receive any treatment, tuberculosis process moved into a generalized form with overall visceral injury (groups 1 and 2).

Although any mechanism offered to explain the mechanism of the complex compound action should not be regarded as restrictive, it is most likely that antimicrobial activity of ABA is related to: a) the structure of biologically active carbohydrates and peptides; b) oxidizing action of iodine molecules both on the cell membrane, and on the cell structure in diffusion of the active substance through the membrane of bacterial cell; c) halogenation of DNA of microorganisms; d) interferons induction in the course of impact of complex compound on immunocompetent cells; e) activation of monocytes-macrophages and cytotoxic T-lymphocytes.

ABA studied after the Examples 1-9 in vitro have a greater or lesser virucidal activity against influenza, herpes and HIV-1 immunodeficiency viruses (Tables 9-13).

In the studies of FS-1 antiviral action in vitro on subinoculated cell cultures, anti-HIV activity of FS-1 was identified in cell culture against laboratory strain of HIV-1 (LAI). The decline in infectivity indices for HIV virus—p24 content and reverse transcriptase—after the drug-induced action indicates the virusocidal action of the drug against human immunodeficiency virus. Application of FS-1 at doses of 0.188 mg/ml and 0.094 mg/ml, or azidothymidine in a dose of 0.01 mg/ml resulted in a significant decrease in extinction as compared to placebo and, consequently, a decrease of p24 protein of human immunodeficiency virus (infectivity index for the virus) by 60 times (Table 12).

Application of FS-1 at doses of 0.094 mg/ml and 0.188 mg/ml, decreased the content of reverse transcriptase—infectivity index for the virus—compared with negative control by 4.1 and 12.7 times. On application of azidothymidine as a positive control at a dose of 0.01 mg/nil, this figure dropped by 5 times only (Table 13).

Antiviral activity of the drug FS-1 against influenza virus A/FPV/Rostock/34 has been established in vitro and in vivo (Tables 14-16).

Thus, survival rate of chickens infected with influenza virus at a dose of 100 $EID_{50}$/0.1 ml after prophylactic use of the drug FS-1 at doses of 0.290 mg/kg and 1.458 mg/kg was 100%, and after prophylactic use of rimantadine—28±12.53%. All control chickens that received saline solution died (100% mortality).

Studies of cytotoxicity and efficacy of ABA in Examples 1-9 have identified three main compounds that were tested with a view of acute toxicity. Toxicological studies were conducted in laboratory animals in compliance with bioethics standards (Guide for the Care and Use of Laboratory Animals. Washington: National Academy Press. 1996). To establish parameters of acute toxicity (LD50) ABA was administered enterally and parenterally in mice and rats.

Results of acute toxicity of three ABA in enteral and paraenteral routes of administration in outbred mice are shown in Tables 17, 18.

The least toxic substance has proven to be ABA FS-1. In enteral (intragastric) administration to mice and rats, FS-1 lethal effect was not achieved because the maximum amount of drug administered was 1 ml and 5 ml, respectively, while doses were 922 and 496 mg/kg, respectively. Macroscopic studies of the internal organs of dead animals revealed that the cause of death appears to be associated with impaired hemodynamics, which is indirectly confirmed by the development of disseminating inopexia and severe blood fullness in internal organs of the animals that died. By the end of the $14^{th}$ day, no abnormalities in the structure of internal organs and tissues have been detected through pathomorphological studies in surviving animals against the control groucl. In this case, significant injuries of mucous membranes in the gastrointestinal tract were not identified. Cumulation coefficient (Ccum) was 1.85, which according to the international drug toxicity scale corresponds to the parameters of drugs with faint cumulative effect.

Further a study was conducted for chronic toxicity in rats and rabbits with intragastric method of administration for 60 days and 30 days recovery period at doses of 5.0 mg/kg (dose is equivalent to 1/100 of MTD established in rats) and 50 mg/kg (dose equivalent to 1/10 of MTD established in rats).

Chronic administration of the drug at a dose of 5.0 mg/kg caused no deviations from the control group of animals in terms of body weight dynamic, physical, hematological, and biochemical indices of blood and urine. No abnormalities in cardiac cycle have been observed. All animals kept normal macro- and microstructure of the internal organs.

Chronic administration of the drug in rats and rabbits at a dose of 50.0 mg/kg caused the following toxic effects. On the part of blood biochemical parameters there was a slight increase in liver enzymes: alanine transaminase, aspartate aminotransferase, and alkaline phosphatase, as well as components of nitrogen metabolism: creatinine, urea. Some animals were found to have venous plethora, hepatocytes with signs of degenerative changes in the cytoplasm; there were nonerosive petechial hemorrhages observed in the stomach wall. Some animals had small intestine coat swelling. Changes of thyroid gland in animals of this group were very diverse and unique. In general, there has been a decrease in functional activity of thyroid gland due to appearance of large follicles and flattening of epithelium. However, studies conducted on the $90^{th}$ day of the experiment ($30^{th}$ day of recovery period) have shown that the identified biochemical changes and microstructure changes of internal organs were reversible.

Reproductive toxicity was studied in mice. Females before and during pregnancy were administered the medicine after the Example 5 intragastrically and intramuscularly. The research results are presented in Table 19.

It has been established that intragastric administration (before and after pregnancy) did not result in premature delivery in mice, even when testing the drug in higher doses (100 mg/kg).

Embryotoxicity study was carried out in chicken embryos. It has shown that ABA doses after the Example 5, up to 12.5 mg/nil, do not have a pathological effect on embryos' development at different stages.

In the study of carcinogenic activity of the drug after the Example 5 (FS-1) a battery of tests was used, which included: identification of genotoxic activity in SOS Chromotest for *E. coli* Ec 1000 (PJ E 43); identification of single-strand DNA breaks and determination of the repair (unscheduled) DNA synthesis in blood cells and cell culture of rhabdomyosarcoma in concentrations ranging from 1 to 2000 µg/ml. Results of studying carcinogenic activity of FS-1 are presented in Table 20. In the conditions used the tested FS-1 is not a SOS response inducer in cells of tester strain of *E. coli* Ec 1000 (PJE43).

A negative result was identified (absence of single-strand DNA breaks) when exposed to 200, 300, 600 µg/ml of FS-1.

Genotoxic activity of the drug after the Example 5 was studied in the induction test of unscheduled (reparative) DNA synthesis in cells of donor's peripheral blood. It was shown that in the concentration range of 50, 100, 200 µg/ml there is no stimulation of unscheduled synthesis detected, whether with metabolic activation or without it.

In the experiments, both without metabolic activation, and with metabolic activation, during Ames test no significant changes in growth activity of all four mutagenic strains of *Salmonella thyphymurium* being studied were detected after the influence of FS-1 as compared with the negative control.

At that this lack of effect on growth of mutagenic strains was registered for its relatively high concentrations as well, such as 1.0 and 2.0 mg/curl. Therefore, FS-1 is not mutagenic in relation to DNA of histidine auxotrophic strains of *Salmonella thyphymurium* in Ames test.

Analysis of FS-1 DNA-damaging effect for both mouse lymphoma L5178Y cells, and human hepatoma HepG2 cells revealed no significant increase of spontaneous formation of comet (tailed) DNA in the cells of these lines. Moreover, the absence of the drug inducing effect on formation of comet (tailed) DNA in the cytoplasm of both types of studied cell lines was also revealed in the presence of metabolic activation by liver enzymes in mice. Consequently, the drug in the studied range of concentrations, even in such large ones as 1.0 and 2.0 mg/ml, has no damaging effect on eukaryotic DNA, in vitro, both in the absence, and following its metabolic activation.

Table 21 presents the results of cytogenetic activity studying. No statistically significant differences in the level of bone marrow leukocytes with chromosomal aberrations were detected, and no quantity and quality of chromosomal aberrations in them after the influence of a single administration of FS-1 in a dose of 22 mg/kg of animal weight was found. Moreover, the repeated administration of FS-1 in a dose of 8 mg/kg of animal weight was also characterized by lack of its impact on both the number and character of chromosomal aberrations in bone marrow leukocytes as compared with control (Table 21).

Therefore, FS-1 in the investigated doses has no damaging effect on eukaryotic DNA in vivo.

Data presented in Table 22 shows that after the single FS-1 administration in a dose of 22 mg/kg of animal weight there is no increase in the content of polychromatic and normochromatic bone marrow erythrocytes with micronuclei, and in the number of micronuclei in them. Additionally, the repeated drug administration at a dose of 8 mg/kg of animal weight is also characterized by the absence of its effect both on the number of polychromatic and normochromatic erythrocytes containing micronuclei, and on the total number of micronuclei in erythrocytes compared with control (Table 22).

Consequently, the medicinal agent in the investigated doses has no damaging effect on eukaryotic DNA, in particular a release of part of DNA from nucleus in the form of micronucleus, in vivo in the course of their normal development.

The results of the experiment on the studying induction of dominant lethal mutations by FS-1 in germ cells have demonstrated that the level of postimplantation losses in animals exposed to the drug through its intramuscular injection at a dose of 22 mg/kg (test group 1.1-1.3) of animal weight, did not change as compared with the control group (Table 23).

Therefore, FS-1 when administered into a body in investigated doses, does not induce development of dominant lethal mutations in germ cells (mature sperm cells, late and early spermatids) in mammals in vivo, i.e. it has no mutagenic activity in the test for dominant lethal alleles.

Results of numerous experiments on the testing FS-1 mutagenic activity in testing systems with different sensitivity, both in vitro, and in vivo, have demonstrated that the drug is not mutagenic, even in its significant quantities. This indicates that FS-1 in its interaction with eukaryotic cells, including actively dividing and germ cells, which belong to the category of highly susceptible, does not have a DNA-damaging and specific mutagenic effects on them, i.e. it does not cause DNA damage and/or dysfunctions in the normal implementation of genetic apparatus.

In the event of ionizing radiation dose exposure, namely, 800 R, in the group of mice that received 0.15 ml of FS-1 prior to irradiation a certain radioprotector effect was achieved. So, while in the control group by the end of 30 days a survival rate was 30%, and mean lifetime 18.9±0.4 days, in the experimental group these figures were 70% and 24.6±0.7 days respectively. Statistical analysis of the results (mean lifetime) using Student's t test has shown a significant difference (30%) in respect of mean lifetime (p<0.05).

Figure 12:
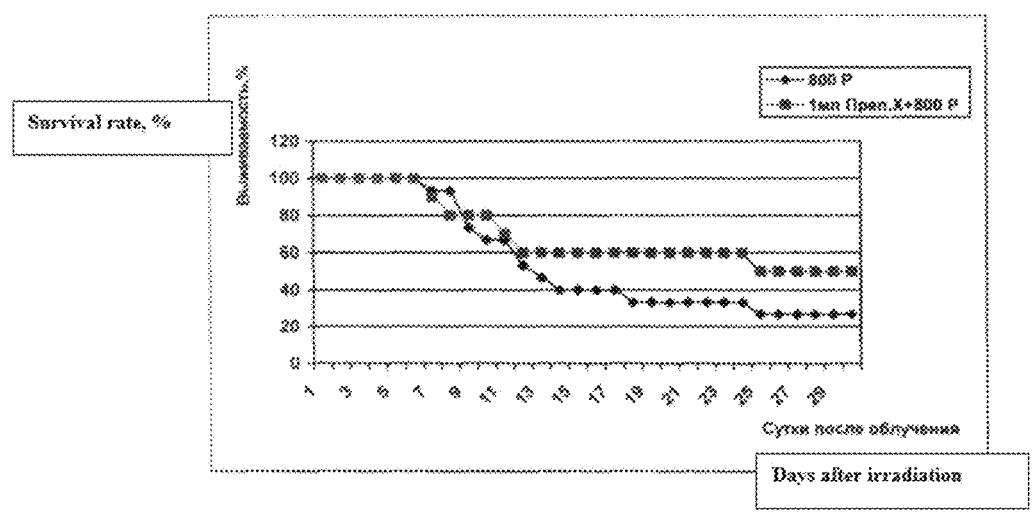
FIG. 12 demonstrates the dynamics of survival of rats in the control and experimental groups during 30 days after irradiation: 1) at irradiation dose of 800 R; 2) at irradiation dose of 800 R against the HRP oral administration (1.0 ml) 30 minutes before irradiation according to a specific example embodiment of the disclosure.

In an experiment in rats at a dose of 800 R at the end of observation period 26.7% of rats survived, and mean lifetime in this group was 17.2±0.5 days. In rats, who before exposure to 800 R dose, received intragastrically 1.0 ml of FS-1, survival rate was 50%, and mean lifetime lengthened by 24% (21.3±0.8 days) (FIG. 12). And in this case there was a certain radioprotector effect. Statistical analysis of the results (mean lifetime) using Student's t test showed significant difference with respect to mean lifetime (p<0.05). Comparing the results of experiments, we can conclude that FS-1 has a certain radioprotective effect which manifests itself in the animals irradiated at doses that are close to semilethal ($LD_{50}$).

According to research made by Venturi (2000), iodine was the first antioxidant at the dawn of life in our planet, which has played an enormous role in human evolution. It is well known that the main damaging radiation factor is free radicals formed in the body immediately after irradiation (Bacq, 1965; Alexander, Bacq, 1974; Halliwell, 1985, 1991). Antioxidants, including iodine, bind free radicals, preventing their interaction with biomolecules of the body (Shimoi, 1996; Halliwell, 1985, 1991).

Effectiveness of therapeutic action of medicinal agent based on ABA after the Example 5 (FS-1) has been established in clinical trials in three groups of volunteer patients with MDR pulmonary tuberculosis (Table 24).

The first group (n=19) received a combined therapy with anti-TB drugs of Type H, as well as ABA after the Example 5 in a dose of 0.1 ml/kg of body weight. The second group (n=17) received anti-TB drugs of Type II, and placebo in a dose of 0.1 ml/kg of body weight; the third group (n=19) received anti-TB drugs of Type II and FS-1 in a dose of 0.125 ml/kg of body weight. All drugs were administered once daily.

Drug safety study based on hemostasis (APTT, prothrombin index, thrombin time, fibrinogen) during the $1^{st}$ month of complex treatment of patients with resistant pulmonary tuberculosis has shown that FS-1 in the used doses of 0.1 and 0.125 mg/kg had no effect on blood coagulation. Moreover, thyroid ultra sound examination after one month of therapy did not detect any kinds of changes in the subjects.

According to the drug susceptibility testing of *Mycobacterium tuberculosis* the resistance to TB drugs (hereinafter—TBD) of Type I (isoniazid (H), rifampicin (R), ethambutol (E), streptomycin (S)) has been proven. Patients were randomized into 3 groups: group 1 (primary) received TBD of Type II (cycloserine (Cs), ofloxacin (Ofs), PAS, protionamid (Pto), capriomicine (Cm))+FS-1 (0.1 ml/kg); group 2 (primary) received TBD of Type II (cycloserine (Cs), ofloxacin (Ofs), PAS (Pas), protionamid (Pto), Capriomicin (Cm))+FS-1 (0.125 ml/kg); group 3 (control) received TBD of Type II (cycloserine (Cs), ofloxacin (Ofs), PAS (Pas), protionamid (Pto), capriomicin (Cm))+placebo).

The average age of subjects was 33.14±9.03 (years), among them—75.8% men and 24.2%—women. Among clinical forms the most frequent form was infiltrative—70.1%, less frequent—fibrocavernous—28.2%. The groups were homogeneous, no significant differences in background characteristics were observed.

Preliminary study of therapeutic efficacy of the drug indicates that smear conversion was significantly higher in the primary groups starting from the $3^{rd}$ month of therapy, which proves the efficacy of FS-1 in combination therapy (Table 28).

The data presented in Table 29 also show that starting from the $3^{rd}$ month of therapy a negative culture is significantly higher in the primary groups compared to the control one, which proves FS-1 efficiency in TB treatment.

The classical method for sputum inoculation of solid medium (Table 30) also suggests that in patients with resistant TB receiving FS-1 in combination with anti-TB drugs of Type II, the specific weight of bacterial examination with negative results was significantly higher compared with control after two months of therapy, which can be traced also after 3 and 4 months.

Changes in X-ray patterns of MDR tuberculosis patients receiving FS-1 in combination with anti-TB drugs of Type II suggest that as early as after one month of therapy, the positive dynamics was significantly higher than in the control group (placebo+TBD, type II), that is, the resorption of infiltration, induration of focuses, and regression of cavities (Table 31) start earlier.

As can be seen in Table 32, there is a weight gain observed in the main group, whereas in the control group, on the contrary, the weight is decreased, and after 3 months the significant changes in body weight are evident in group 1 and group 2, and after 4 months—in group 3.

Preliminary results of Phase II clinical trials prove the efficacy of FS-1 application in the combined antiphthisic therapy in patients with MDR TB.

TABLE 1

ABA composition

| Example No. | Compound | $I_2$, g/L | KI, g/L | Carbohydrate, g/L | Protein Albumin, g/L | IL-2, mg/L | PVA, g/L | LiCl, g/L | NaCl, g/L | $CaCl_2$, g/L | $MgCl_2$, g/L | Ionic strengh |
|---|---|---|---|---|---|---|---|---|---|---|---|---|
| 1 | FS-1.1 | 0.82 | 1.2 | 130.0 | 5.0 | — | 3.0 | 3.96 | 5.0 | 1.98 | 8.4 | 13.6 |
| 2 | FS-1.2 | 2.0 | 3.0 | 108.3 | 4.17 | — | 2.5 | 3.3 | 4.17 | 1.65 | 7.0 | 13.2 |
| 3 | FS-1.3 | 4.1 | 6.0 | 72.0 | 2.8 | — | 1.7 | 2.2 | 2.8 | 1.1 | 4.66 | 10.8 |
| 4 | FS-1.4 | 4.1 | 6.0 | 72.0 | — | — | 1.7 | — | — | — | — | 3.02 |
| 5 | FS-1 | 8.2 | 12.1 | 130.0 | 5.0 | — | 3.0 | 4.0 | 5.0 | 2.0 | 8.4 | 20.60 |
| 6 | FS-1.5 | 34.0 | 50.5 | 24.1 | — | — | 2.8 | — | — | — | — | 25.3 |
| 7 | FS-1.6 | 34.0 | 50.5 | 24.1 | 0.93 | — | 2.8 | 0.73 | 0.93 | 0.37 | 1.55 | 27.9 |
| 8 | FS-1.7 | 8.2 | 12.1 | 130.0 | 5.0 | 0.6 | 3.0 | 4.0 | 5.0 | 2.0 | 8.4 | 20.60 |
| 9 | FS-1.8 | 74.5 | 110.0 | 13.1 | 0.51 | — | 3.0 | 0.4 | 0.5 | 0.2 | 0.84 | 56.3 |

TABLE 2

Output of complex $Mg^{2+}{}_{n4}I_{3}{}^{-}{}_{n6}$ depending on $I_2$ excess compared to the stoichiometric content, %

| | | | |
|---|---|---|---|
| Calculated | 78 | 86 | 94 |
| Experimental | 74 | 82 | 93 |
| $I_2$ excess from OT | 0 | 20 | 50 |

TABLE 3

Output of complex $Ca^{2+}{}_{n5}I_{3}{}^{-}{}_{n7}$ depending on $I_2$ excess compared to the stoichiometric content, %

| | | | |
|---|---|---|---|
| Calculated | 71 | 82 | 89 |
| Experimental | 68 | 76 | 85 |
| $I_2$ excess from OT | 0 | 20 | 50 |

TABLE 4

Spatial (lengths of coordination bonds (Å)) and energy (stabilization energy $\Delta E$, kcal/mol) characteristics of I-IV complexes.

| | I | II | III | IV |
|---|---|---|---|---|
| Li—I | 2.93 | 2.96 | 2.97 | 2.80 |
| N(O)—I | 2.46 | 2.40 | 2.76 | 2.18 |
| I—I | 2.76 | 2.82 | 2.72 | 3.03 |
| $-\Delta E$ | 16.60 | 14.26 | 6.25 | 24.25 |

TABLE 5

CC 50 and MNC for different series of the substance FS-1 in MDCK cell culture after 72-hour incubation

| Drug name | Drug dilutions | |
|---|---|---|
| | CC 50 | MNC |
| FS-1 | 1:20 | 1:80 |
| ABA-1 | 1:50 | 1:100 |
| ABA-2 | 1:800 | 1:3200 |
| ABA-3 | 1:100 | 1:200 |
| ABA-4 | 1:50 | 1:6400 |
| ABA-5 | 1:1460 | 1:3200 |
| ABA-6 | 1:5063 | 1:6000 |
| ABA-7 | 1:565 | 1:1500 |
| ABA-8 | 1:3637 | 1:6400 |

TABLE 6

Bactericidal activity against microorganisms of different pathogenicity groups

| Microorganism name | Minimum inhibitory concentration of the complex compound after the Example, mg/ml | | | | | | | | |
|---|---|---|---|---|---|---|---|---|---|
| | 1 | 2 | 3 | 4 | 5 | 6 | 7 | 8 | 9 |
| *Escherichia coli* INMIA 5002 (ATCC 11303) | 2.5 | 1 | 1 | 1 | 1 | 2.5 | 1 | 1 | 2.5 |
| *Escherichia coli* INMIA 5230 | 2.5 | 1 | 1 | 1 | 1 | 2.5 | 1 | 1 | 2.5 |
| *Staphylococcus aureus* INMIA 5233 | 2.5 | 1 | 1 | 1 | 1 | 5 | 1 | 1 | 2.5 |
| *Serratia marcescens* INMIA 5251 (ATCC 9986. Bu 211. IFO 3736) | 2.5 | 1 | 1 | 1 | 2.5 | 5 | 1 | 1 | 2.5 |
| *Mycobacterium* spp INMIA 5237 (штамм B-5) | 7 | 1 | 1 | 1 | 0.0437 | 7 | 1 | 1 | 7 |
| *Pseudomonas fluorescens* INMIA 5248 (ATCC948. CCEB 295) | 2.5 | 1 | 1 | 1 | 0.5 | 2.5 | 1 | 1 | 2.5 |
| *Bacillus subtilis* INMIA 1820 (ATCC 6633) | 1 | 1 | 1 | 1 | 0.5 | 1 | 1 | 1 | 1 |
| *Bacillus cereus* INMIA 2111 (ATCC 11778) | 30 | 30 | 10 | 10 | 0.5 | 30 | 10 | 30 | 30 |
| *Bacillus coagulans* INMIA 1906 (Bu156. NCIB 8041) | 10 | 10 | 10 | 10 | 0.5 | 10 | 10 | 10 | 10 |
| *Candida albicans* INMIA 8013 | 5 | 5 | 30 | 5 | 1 | 5 | 5 | 10 | 10 |
| *Kloeckera brevis* INMIA 8018 | 5 | 1 | 1 | 5 | 1 | 5 | 1 | 10 | 10 |
| *Aspergillus versicolor* VKM F-837 | 10 | 10 | 30 | 10 | 5 | 10 | 10 | 10 | 10 |
| *Aspergillus flavus* INMIA 8134 (VKM F-747) | 10 | 10 | 30 | 10 | 5 | 10 | 10 | 10 | 10 |

TABLE 7

The results of combined action of the medicinal agent after the example of a number of susceptible and multiresistant strains of *Mycobacterium tuberculosis*

| FS-1 the drug 0.0437 mg/ml | | Concentration of anti-tuberculosis drug | | | | | | | |
|---|---|---|---|---|---|---|---|---|---|
| | | H (µg/ml) | | S (µg/ml) | | E (µg/ml) | | R (µg/ml) | |
| | Strains | 1.0 | 5.0 | 5.0 | 10.0 | 2.0 | 5.0 | 40.0 | K |
| FS-1 | 6* | s | s | s | s | s | s | s | +++ |
| without FS-1 | | r | r | r | r | r | r | r | +++ |
| FS-1 | 1* | s | s | s | s | s | s | s | +++ |

TABLE 7-continued

The results of combined action of the medicinal agent after the example of a number of susceptible and multiresistant strains of *Mycobacterium tuberculosis*

| FS-1 the drug 0.0437 mg/ml | Strains | Concentration of anti-tuberculosis drug | | | | | | | K |
|---|---|---|---|---|---|---|---|---|---|
| | | H (µg/ml) 1.0 | 5.0 | S (µg/ml) 5.0 | 10.0 | E (µg/ml) 2.0 | 5.0 | R (µg/ml) 40.0 | |
| without FS-1 | | r | r | r | r | r | r | r | +++ |
| FS-1 | 7* | s | s | s | s | s | s | s | +++ |
| without FS-1 | | r | r | r | r | r | r | r | +++ |
| FS-1 | 510* | s | s | s | s | s | s | s | +++ |
| without FS-1 | | r | r | r | r | r | r | r | +++ |
| FS-1 | 516* | s | s | s | s | s | s | s | +++ |
| without FS-1 | | r | r | r | r | r | r | r | +++ |
| FS-1 | 517* | s | s | s | s | s | s | s | +++ |
| without FS-1 | | r | r | r | r | r | r | r | +++ |
| FS-1 | 518* | s | s | s | s | s | s | s | +++ |
| without FS-1 | | r | r | r | r | r | r | r | +++ |
| FS-1 | 797* | s | s | s | s | s | s | s | +++ |
| without FS-1 | | r | r | r | r | r | r | r | +++ |
| FS-1 | $H_{37}R_v$ | s | s | s | s | s | s | s | +++ |
| without FS-1 | | r | r | r | r | r | r | r | +++ |

Note:
R—resistant;
S—sensitive;
R—Rifampicin;
H—Isoniasid;
*multidrug-resistant strain;
S—streptomycin;
E—ethambutol;
+++ confluent growth

TABLE 8

Tuberculous lesions in organs of guinea pigs

| Group No. | Time after introduction of infection (days) | Time after beginning of treatment (days) | Number of tuberculous lesions in organs | |
|---|---|---|---|---|
| | | | Lungs | Liver |
| Group 1 | 39 | — | 10 | 12 |
| Control Animals, infected with | 46 | — | 11 | 15 |
| *M. tuberculosis* $H_{37}R_v$ | 53 | — | 26 | 31 |
| | 55 | — | 25 | 34 |
| | 59 | — | 27 | 40 |
| Group 2 | 39 | — | 14 | 11 |
| Control animals infected with | 46 | — | 13 | 14 |
| multiresistant *mycobacterium* | 53 | — | 18 | 14 |
| strains | 57 | — | 27 | 31 |
| | 60 | — | 30 | 42 |
| Group 3 | 39 | 7 | 17 | 18 |
| Test animals injected with | 46 | 14 | 11 | 8 |
| *M. tuberculosis* $H_{37}R_v$ | 53 | 21 | 9 | 7 |
| and treated with TBD | 60 | 28 | 3 | 2 |
| | 67 | 35 | — | — |
| Group 4 | 39 | 7 | 11 | 13 |
| Test animals infected with | 46 | 14 | 10 | 9 |
| *M. tuberculosis* $H_{37}R_v$ and | 53 | 21 | 4 | 7 |
| treated with FS-1 | 60 | 28 | — | — |
| | 65 | 33 | — | — |
| Group 5 | 39 | 7 | 16 | 7 |
| Test animals infected with | 46 | 14 | 6 | 5 |
| *M. tuberculosis* $H_{37}R_v$ and | 53 | 21 | — | — |
| treated with TBD and FS-1 | 60 | 28 | — | — |
| | 67 | 35 | — | — |
| Group 6 | 39 | 7 | 11 | 14 |
| Test animals infected with | 46 | 14 | 14 | 16 |
| multiresistant strains of | 53 | 21 | 21 | 24 |
| *mycobacteria* and treated | 60 | 28 | 20 | 23 |
| with TBD | 67 | 35 | 35 | 27 |
| Group 7 | 39 | 7 | 12 | 14 |
| Test animals infected with | 46 | 14 | 10 | 9 |
| multiresistant strains of | 53 | 21 | 4 | 5 |
| *mycobacteria* and treated | 60 | 28 | 2 | — |
| with FS-1 | 66 | 35 | — | — |
| Group 8 | 39 | 7 | 13 | 17 |
| Test animals infected with | 46 | 14 | 3 | 7 |
| multiresistant strains of | 53 | 21 | — | — |

TABLE 8-continued

Tuberculous lesions in organs of guinea pigs

| Group No. | Time after introduction of infection (days) | Time after beginning of treatment (days) | Number of tuberculous lesions in organs | |
|---|---|---|---|---|
| | | | Lungs | Liver |
| *mycobacteria* and treated with TBD and FS-1 | 60<br>67 | 28<br>35 | —<br>— | —<br>— |

TABLE 9

Haemagglutinin titre of the residual influenza virus HAU

| Substance name | Substance content, mg/ml | Virus dilutions | | | | | | | | Titr., HAU |
|---|---|---|---|---|---|---|---|---|---|---|
| | | 1/2 | 1/4 | 1/8 | 1/16 | 1/32 | 1/64 | 1/128 | 1/256 | |
| 1 | 2 | 3 | 4 | 5 | 6 | 7 | 8 | 9 | 10 | 11 |
| FS-1 | 0.188 | ---- | ---- | ---- | ---- | ---- | ---- | ---- | ---- | 0 |
| | 0.094 | ++++ | ++++ | ---- | ---- | ---- | ---- | ---- | ---- | 4 |
| | 0.047 | ++++ | ++++ | ++++ | ---- | ---- | ---- | ---- | ---- | 8 |
| ABA-1 | 5.0 | ++++ | ++++ | ++++ | ++-- | ---- | ---- | ---- | ---- | 12 |
| | 2.5 | ++++ | ++++ | ++++ | ++-- | ---- | ---- | ---- | ---- | 12 |
| | 1.25 | ++++ | ++++ | ++++ | ++++ | ++-- | ---- | ---- | ---- | 24 |
| ABA-2 | 0.31 | ++++ | ++++ | ++++ | ++++ | ++++ | ---- | ---- | ---- | 32 |
| | 0.16 | ++++ | ++++ | ++++ | ++++ | ++++ | ++-- | ---- | ---- | 48 |
| | 0.08 | ++++ | ++++ | ++++ | ++++ | ++++ | ++-- | ---- | ---- | 48 |
| ABA-3 | 2.5 | ++++ | ++++ | ++++ | ++++ | ++++ | ---- | ---- | ---- | 32 |
| | 1.25 | ++++ | ++++ | ++++ | ++++ | ++++ | ---- | ---- | ---- | 32 |
| | 0.63 | ++++ | ++++ | ++++ | ++++ | ++++ | ++-- | ---- | ---- | 48 |
| ABA-4 | 5.0 | ++++ | ++-- | ---- | ---- | ---- | ---- | ---- | ---- | 3 |
| | 2.5 | ++++ | ++-- | ---- | ---- | ---- | ---- | ---- | ---- | 3 |
| | 1.25 | ++++ | ++++ | ++++ | ++++ | ++++ | ++++ | ---- | ---- | 64 |
| ABA-5 | 0.2 | ++++ | ++++ | ++++ | ++-- | ---- | ---- | ---- | ---- | 12 |
| | 0.1 | ++++ | ++++ | ++++ | ++-- | ---- | ---- | ---- | ---- | 12 |
| | 0.05 | ++++ | ++++ | ++++ | ++++ | ++++ | ++-- | ---- | ---- | 48 |
| ABA-6 | 0.05 | ++++ | ++++ | ++++ | ++++ | ++-- | ---- | ---- | ---- | 24 |
| | 0.025 | ++++ | ++++ | ++++ | ++++ | ++++ | ++-- | ---- | ---- | 48 |
| | 0.01 | ++++ | ++++ | ++++ | ++++ | ++++ | ++-- | ---- | ---- | 48 |
| ABA-7 | 0.4 | ---- | ---- | ---- | ---- | ---- | ---- | ---- | ---- | 0 |
| | 0.2 | ---- | ---- | ---- | ---- | ---- | ---- | ---- | ---- | 0 |
| | 0.1 | ---- | ---- | ---- | ---- | ---- | ---- | ---- | ---- | 0 |
| ABA-8 | 0.06 | ++++ | ++++ | ++++ | ++++ | ---- | ---- | ---- | ---- | 8 |
| | 0.03 | ++++ | ++++ | ++++ | ++++ | ---- | ---- | ---- | ---- | 16 |
| | 0.015 | ++++ | ++++ | ++++ | ++++ | ++-- | ---- | ---- | ---- | 24 |
| Virus control | | ++++ | ++++ | ++++ | ++++ | ++++ | ++++ | ++-- | ---- | 96 |

Note:
++++ - 100% umbrella hemagglutination
+++ - 75% hemagglutination
++ - 50% hemagglutination
++ - 25% hemagglutination
– - - no hemagglutination

TABLE 10

Determination of FS-1 antiviral activity against influenza virus A/FPV/Waybrige/78/H7N7 in MDCK cell culture after 72 hours

| Well number | Active substance content, mg/ml | | | | 0 (Cells control) | 0 (Virus Control) |
|---|---|---|---|---|---|---|
| | 0.038 | 0.019 | 0.009 | 0.005 | | |
| 1 | ----* | ----* | ++-- | +++- | ---- | ++++ |
| 2 | ---- | ---- | ++-- | +++- | ---- | ++++ |
| 3 | ---- | ---- | ++-- | +++- | ---- | ++++ |
| 4 | ---- | ---- | ++-- | +++- | ---- | ++++ |

Notes:
1 * - CPE manifestation degree
2 ++++ - pronounced degradation of cell monolayer.
3 ---- - no cell degradation.

TABLE 11

Determination of FS-1 antiviral activity against herpes simplex virus of I type, "Victory" strain in RD cell culture after 72 hours

| Well number | Active substance content, mg/ml | | | | 0 (контроль клеток) | 0 (контроль вируса) |
|---|---|---|---|---|---|---|
| | 0.038 | 0.019 | 0.009 | 0.005 | | |
| 1 | ----* | ++++ | ++++ | ++++ | ---- | ++++ |
| 2 | ---- | ++++ | +++- | ++++ | ---- | ++++ |

TABLE 11-continued

Determination of FS-1 antiviral activity against herpes simplex virus of I type, "Victory" strain in RD cell culture after 72 hours

| Well number | Active substance content, mg/ml | | | | 0 (контроль клеток) | 0 (контроль вируса) |
|---|---|---|---|---|---|---|
| | 0.038 | 0.019 | 0.009 | 0.005 | | |
| 3 | ---- | ++-- | +++- | ++++ | ---- | ++++ |
| 4 | ---- | +--- | +++- | ++++ | ---- | ++++ |

Notes:
1 * - CPE manifestation degree
2 ++++ - pronounced degradation of cell monolayer.
3 ---- - no cell degradation.

TABLE 12

FS-1 virucidal effect on human immunodeficiency virus HIV-1 (LAI) (detection in IFA by the protein p24)

| Drug | Extinction factor |
|---|---|
| Virus control (n = 6) | 2.65517 ± 0.76283 |
| 0.188 mg/ml of FS-1 (n = 5) | 0.04380 ± 0.00086 |
| 0.094 mg/ml of FS-1 (n = 5) | 0.04660 ± 0.000678 |
| 0.01 mg/ml of azidothymidine (n = 5) | 0.04460 ± 0.003187 |
| Cell control (n = 5) | 0.042 ± 0.000400 |

TABLE 13

FS-1 virucidal effect on human immunodeficiency virus HIV-1 (LAI) (detection in IEA by reverse transcriptase)

| Drug | Extinction factor |
|---|---|
| Virus control (n = 5) | 2.884 ± 0.043052 |
| 0.188 mg/ml of FS-1 (n = 5) | 0.2274 ± 0.004094 |
| 0.094 mg/ml of FS-1 (n = 5) | 0.7072 ± 0.012464 |
| 0.01 mg/ml of azidothymidine (n = 5) | 0.5724 ± 0.005464 |
| Cell control (n = 5) | 0.2168 ± 0.000583 |

TABLE 14

Determination of FS-1 antiviral activity in vitro against influenza virus A/FPV/Waybrige/78/H7N7 in MDCK cell culture after 72 hours

| Well number | Active substance content, mg/ml | | | | 0 (Cells control) | 0 (Virus Control) |
|---|---|---|---|---|---|---|
| | 0.038 | 0.019 | 0.009 | 0.005 | | |
| 1 | ----* | ---- | ++-- | +++- | ---- | ++++ |
| 2 | ---- | ---- | ++-- | +++- | ---- | ++++ |
| 3 | ---- | ---- | ++-- | +++- | ---- | ++++ |
| 4 | ---- | ---- | ++-- | +++- | ---- | ++++ |

Notes:
1 * - CPE manifestation degree
2 ++++ - pronounced degradation of cell monolayer.
3 ---- - no cell degradation.

TABLE 15

FS-1 preventive effect in vivo in a model of influenza virus strain A/FPV/Rostock/34

| Drug (dose for 1 kg of body weight) | Total number of chickens | Number of survived chickens | Number of chickens that died | Survival % |
|---|---|---|---|---|
| Saline solution | 14 | 0 | 14 | 0 |
| 0.290 mg/ml of FS-1 | 14 | 14 | 0 | 100 |
| 1.458 mg/ml of FS-1 | 14 | 14 | 0 | 100 |
| 8.33 mg/ml of Rimantadine | 14 | 4 | 10 | 28.6 ± 12.53 |

TABLE 16

FS-1 therapeutic effect in vivo in a model of influenza virus strain A/FPV/Rostock/34

| Drug (dose for 1 kg of body weight) | Total number of chickens | Number of survived chickens | Number of chickens that died | Survival % |
|---|---|---|---|---|
| Saline solution | 14 | 0 | 14 | 0 |
| 0.290 mg/ml of FS-1 | 14 | 6 | 8 | 42.9 ± 13.73 |
| 1.458 mg/ml of FS-1 | 14 | 14 | 0 | 100 |
| 8.33 mg/ml of Rimantadine | 14 | 6 | 8 | 42.9 ± 13.73 |

TABLE 17

| Acute toxicity characteristics (LD50 mg/kg) | | |
|---|---|---|
| Example | Mice | Rats |
| Enteral route of administration | | |
| ABA | 330 | 243 |
| ABA | 579.25 | 360.5 |
| ABA (FS-1) | n.d. | n.d. |
| Parenteral route of administration | | |
| ABA | 65 | 48 |
| ABA | 106 | 75 |
| ABA (FS-1) | 213 | 100 |

N.d.—not detected

TABLE 18

Results of studying FS-1 cumulative toxicity in mice

| FS-1 dose (mg/kg) | Number of animals that died | Total number of animals in the group |
|---|---|---|
| 9.51 | 0 | 10 |
| 14.27 | 0 | 10 |
| 21.40 | 2 | 10 |
| 32.06 | 6 | 10 |
| 48.13 | 8 | 10 |
| 72.24 | 9 | 10 |
| 108.40 | 10 | 10 |

TABLE 19

Results of studying ABA FS-1 fetal toxicity

| Experimental groups | Dose, mg/kg | Effect (death rate or premature labor) |
|---|---|---|
| intramuscularly | 100 | Prenature labor, unviable fetus |
| intramuscularly | 25 | 0 |
| intramuscularly | 6.25 | 0 |
| (control) | phosphate buffer | 0 |
| per os | 100 | 0 |
| per os | 25 | 0 |
| per os | 6.25 | 0 |
| (control) | phosphate buffer | 0 |

TABLE 20

Results of studying FS-1 carcinogenic action

| Test | FS-1 "ineffective" concentrations, µg/ml | FS-1 toxic concentrations |
|---|---|---|
| SOS Chromotest, E. coli | 1-1000 | — |
| Single-strand DNA breaks, RD cells | 200-600 | 1200-2000 |
| Induction of unscheduled (reparative) DNA synthesis, human lymphocytes | 50-200 | 400-800 |

TABLE 21

Structural damage of chromosomes in white blood cells of bone marrow of mice exposed to FS-1

| | Type of chromosome aberration | | | | | | | |
|---|---|---|---|---|---|---|---|---|
| | $N_f$ | | | | | $N_M$ | $N_{CD}$ | |
| Group | $N_{find}$ M ± SD | $N_{fp}$ M ± SD | $N_{exg}$ M ± SD | $N_g$ M ± SD | $N_{cb}$ M ± SD | (%) M ± SD | (%) M ± SD | $N_t$ (%) M ± SD |
| Control 1 | 3.67 ± 1.03 | 0 | 0 | 0 | 0 | 0 | 0 | 1.33 ± 0.52 |
| Control 2 | 3.00 ± 0.89 | 0 | 0 | 0 | 0 | 0 | 0 | 1.67 ± 0.47 |
| Control 3 | 6.00 ± 1.26 | 4.17 ± 0.75 | 2.33 ± 0.52 | 3.33 ± 1.03 | 4.83 ± 0.40 | 5.00 ± 0.63 | 2.33 ± 0.52 | 15.50 ± 2.17 |
| Control 4 | 7.17 ± 1.47 | 3.67 ± 0.81 | 3.67 ± 0.52 | 4.17 ± 0.98 | 2.67 ± 0.82 | 8.00 ± 1.09 | 3.83 ± 0.75 | 21.67 ± 3.26 |
| 8 mg/kg | 3.00 ± 1.26 | 0 | 0 | 0 | 0 | 0 | 0 | 1.83 ± 0.41 |
| 22 mg/kg | 4.00 ± 0.63 | 0 | 0 | 0 | 0 | 0 | 0 | 2.17 ± 0.41 |

Notes:
$N_f$—number of fragments,
$N_{find}$—number of individual fragments,
$N_{fp}$—number of paired fragments;
$N_{exg}$—number of exchanges;
$N_g$—number of gaps;
$N_{cb}$—number of breaks in centromere,
$N_M$—number of cells with multiple disorders;
$N_{CD}$—number of cells with complete chromosome destruction;
$N_t$—total number of cells with aberrations.

TABLE 22

Structural damages in polychromatic and normochromatic bone marrow erythrocytes of mice exposed to FS-1

| Group | $N_{PCE}$ (%) M ± SD | $N_{MPCE}$ M ± SD | NNCE (%) M ± SD | $N_{MNCE}$ M ± SD |
|---|---|---|---|---|
| Control 1 | 0.18 ± 0.08 | 2.67 ± 1.37 | 0.05 ± 0.05 | 0.67 ± 0.82 |
| Control 2 | 0.25 ± 0.10 | 3.17 ± 0.98 | 0.07 ± 0.05 | 0.83 ± 0.75 |
| Control 3 | 4.48 ± 0.67 | 93.83 ± 11.87 | 0.98 ± 0.13 | 21.67 ± 2.94 |
| Control 4 | 6.43 ± 0.80 | 123.00 ± 8.51 | 1.38 ± 0.15 | 28.83 ± 3.19 |
| 8 mg/kg | 0.30 ± 0.11 | 3.50 ± 1.38 | 0.07 ± 0.05 | 0.83 ± 0.75 |
| 22 mg/kg | 0.37 ± 0.12 | 4.50 ± 1.38 | 0.10 ± 0.06 | 1.33 ± 1.03 |

Notes:
$N_{PCE}$—number of polychromatic erythrocytes with micronucleous in cytoplasm;
$N_{MPCE}$—number of micronuclei per 1000 of polychromatic erythrocytes;
$N_{NCE}$—number of normochromatic erythrocytes with micronuclei in cytoplasm;
$N_{MNCE}$—number of micronuclei per 1000 of normochromatic erythrocytes.

TABLE 23

Study of FS-1 inducing action on the development of dominant lethal mutations in germ cells (sperm cells) of mice

| Stage of spermatogenesis | Group | $N_O$ | Npf | F (%) | Ipil M ± SD |
|---|---|---|---|---|---|
| Mature sperm cells | Control 1.1 | 30 | 27 | 90.00 | 0.06 ± 0.01 |
|  | Control 2.1 | 30 | 18 | 60.00 | 0.26 ± 0.01 |
|  | Experimental 1.1 | 30 | 23 | 76.67 | 0.08 ± 0.02 |
| Late spermatids | Control 1.2 | 30 | 25 | 83.33 | 0.06 ± 0.01 |
|  | Control 2.2 | 30 | 20 | 66.67 | 0.15 ± 0.01 |
|  | Experimental 1.2 | 30 | 27 | 90.00 | 0.07 ± 0.01 |
| Early spermatids | Control 1.3 | 30 | 26 | 86.67 | 0.08 ± 0.01 |
|  | Control 2.3 | 30 | 23 | 76.67 | 0.12 ± 0.01 |
|  | Experimental 1.3 | 30 | 27 | 80.00 | 0.06 ± 0.01 |

Note:
$N_O$—total number of females;
Npf—number of pregnant females;
F—fertility;
Ipil—postimplantation loss index.

TABLE 24

Main characteristics of the subjects

| | Tested drug and dosage groups | | |
|---|---|---|---|
| Parameters | FS-1 0.1 ml/kg | Placebo 0.1 ml/kg | FS-1 0.125 ml/kg |
| 1 | 2 | 3 | 4 |
| Number of subjects | 19 | 17 | 19 |
| Mean age (standard deviation) | 32.5 ± 8.5 | 31.24 ± 6.4 | 34.9 ± 10.9 |
| Gender (males, %; females, %) | 78.95%; 21.05% | 70.59%; 29.41% | 78.95%; 21.05% |
| Clinical forms (infiltrative, %; fibrocavernous, %) | 78.95%; 21.05% | 70.59%; 29.41% | 78.95%; 21.05% |
| Process prevalence (single-sided, %; two-sided, %) | 55.5%; 44.5% | 41.2%; 58.8% | 68.4%; 31.6% |
| Distribution according to the disease duration (less than 1 year, %; more than 1 year, %) | 66.70%; 33.30% | 47.05%; 52.95% | 42.10%; 57.89% |

TABLE 25

Comparative average statistical APTT rates (s)

| Points | 1 (primary) group (n = 12) M ± m | 2 (control) group (n = 12) M ± m | 3 (primary) group (n = 7) M ± m |
|---|---|---|---|
| Initial | 40.15 ± 8.01 | 43.31 ± 7.10 | 43.63 ± 4.22 |
| 1 month | 43.83 ± 4.67 | 49.08 ± 8.56 | 29.29 ± 8.24 |

TABLE 26

Comparative average statistical rates of prothrombin index (%)

| Points | 1 (primary) group (n = 12) M ± m | 2 (control) group (n = 12) M ± m | 3 (primary) group (n = 7) M ± m |
|---|---|---|---|
| Initial | 81.0 ± 8.77 | 77.46 ± 8.28 | 82.13 ± 16.91 |
| 1 month | 83.17 ± 8.36 | 87.69 ± 8.02 | 86.0 ± 13.14 |

TABLE 27

Comparative average statistical rates of thrombin clotting time (s)

| Points | 1 (primary) group (n = 12) M ± m | 2 (control) group (n = 12) M ± m | 3 (primary) group (n = 7) M ± m |
|---|---|---|---|
| Initial | 16.1 ± 4.06 | 16.34 ± 2.44 | 21.88 ± 5.06 |
| 1 month | 19.58 ± 1.25 | 23.46 ± 2.88 | 24.43 ± 2.08 |

Note:
Statistically significant differences with initial rates:
* $p < 0.05$;
** $p < 0.01$;
*** $p < 0.001$

TABLE 28

Smear conversion dynamics, %

| Groups | 1 month | 2 months | 3 months | 4 months | 5 months | 6 months |
|---|---|---|---|---|---|---|
| Group 1 | 42.3 | 62.5 | 63.15* | 82.3* | 78.6* | 77.7* |
| Group 2 | 70 | 47.8 | 47.6* | 88.9* | 78.6* | 100* |
| Group 3 (control) | 50 | 58.3 | 28.5* | 53.3* | 53.8* | 50* |

Note:
*$p < 0.025$;
**$p < 0.001$

TABLE 29

Comparative data on lack of growth among colonies from sputum in liquid medium, %

| Groups | 1 month | 2 months | 3 months | 4 months | 5 months |
|---|---|---|---|---|---|
| Group 1 | 62.5 | 55 | 77.7* | 82 | 100* |
| Group 2 | 40 | 55 | 81.3* | 90* | 100* |

TABLE 29-continued

Comparative data on lack of growth among colonies from sputum in liquid medium, %

| Groups | 1 month | 2 months | 3 months | 4 months | 5 months |
|---|---|---|---|---|---|
| Group 3 (control) | 42.85 | 61.1 | 68.7* | 80 | 88.8* |

Note:
*$p < 0.025$;
**$p < 0.001$

TABLE 30

Comparative data on lack of growth among colonies from sputum in dense medium, %

| Groups | 1 month | 2 months | 3 months | 4 months |
|---|---|---|---|---|
| Group 1 | 69.56 | 94.7* | 100** | 100** |
| Group 2 | 58.3 | 84.2* | 100** | 100** |
| Group 3 (control) | 63.6 | 66.6* | 75* | 70** |

Примечание:
*$p < 0.025$;
**$p < 0.001$

TABLE 31

Comparative data of radiological pattern dynamics

| Groups | 1 month | 2 months | 3 months | 4 months | 5 months | Groups |
|---|---|---|---|---|---|---|
| Group 1 | 80* | 100*** | 100*** | 92.9** | 92.3** | 85.7* |
| Group 2 | 92* | 95.5*** | 100*** | 93.3** | 100*** | |
| Group 3 (control) | 63.2* | 52.4*** | 53.8*** | 70** | 62.5** | 71.4* |

Note:
*$p < 0.05$;
**$p < 0.025$;
****$p < 0.005$

TABLE 32

Comparative average statistical indicators of body weight dynamics within 1 month of therapy

| Groups and doses | FS-1, 0.1 ml/kg | | FS-1, 0.125 ml/kg | | Placebo | |
|---|---|---|---|---|---|---|
| | n | M ± m | n | M ± m | n | M ± m |
| initial | 28 | 59.04 ± 11.23 | 26 | 59.40 ± 9.95 | 26 | 57.85 ± 10.37 |
| 1 month | 21 | 59.57 ± 12.15 | 19 | 61.83 ± 10.51 | 19 | 57.96 ± 11.28 |
| 2 months | 20 | 61.77 ± 11.29 | 17 | 57.34 ± 11.15 | 17 | 57.34 ± 11.15 |
| 3 months | 16 | 63.1 ± 12.05* | 15 | 64.19 ± 11.88* | 14 | 54.56 ± 8.79 |
| 4 months | 11 | 59.89 ± 9.33 | 8 | 63.57 ± 10.72* | 10 | 53.26 ± 6.87 |
| 5 months | 9 | 62.91 ± 9.41 | | — | 8 | 54.86 ± 7.93 |

Note:
*$P < 0.05$;
**$P < 0.01$;
***$P < 0.001$

The invention claimed is:

1. A method for producing an antimicrobial ionic nanostructured complex, the method comprising:
   (a) combining carbohydrate selected from amylopectin, dextran, or dextrin with a salt mixture comprising an alkali metal salt selected from sodium chloride and lithium chloride, and an alkaline earth metal salt selected from magnesium chloride and calcium chloride in an aqueous medium to form an intermediate composition A;
   (b) combining albumin with a salt mixture comprising an alkali metal salt selected from sodium chloride and lithium chloride, and an alkaline earth metal salt selected from magnesium chloride and calcium chloride to form an intermediate composition B;
   (c) combining the intermediate composition A with the intermediate composition B to form an intermediate composition C,
   (d) combining the intermediate composition C with potassium polyiodide, prepared by mixing iodine ($I_2$) and potassium iodide, to form the first ionic nanostructured complex (product D) in an aqueous medium,
   wherein the first ionic nanostructured complex comprises an intercalated iodine, and wherein the aqueous medium has an ionic strength from about 3.0 to about 56.3 (moles per liter or moles per kilogram).

2. The method of claim 1 further comprising the steps of:
   (e) combining the first ionic nanostructured complex (product D) with an intermediate composition B, which intermediate composition B is produced by combining albumin with a salt mixture comprising an alkali metal salt selected from sodium chloride and lithium chloride, and an alkaline earth metal salt selected from magnesium chloride and calcium chloride, and combine with an interleukin to form an intermediate mixture E; and
   (f) combining intermediate mixture E with a potassium polyiodide, prepared by mixing iodine ($I_2$) and potassium iodide, to form a second ionic nanostructured complex (product F), wherein the second ionic nanostructured complex comprises an intercalated iodine.

3. The method according to claim 2, wherein the interleukin is interleukin 2.

4. The method according to claim 1, wherein the aqueous medium comprises dioxane.

5. The method according to claim 2, wherein the aqueous medium comprises dioxane.

6. The method according to claim 1, wherein the aqueous medium further comprises polyvinyl alcohol.

7. The method according to claim 2, wherein the aqueous medium further comprises polyvinyl alcohol.

8. The method according to claim 3, wherein the aqueous medium further comprises polyvinyl alcohol.

* * * * *